United States Patent
Park et al.

(10) Patent No.: US 10,307,117 B2
(45) Date of Patent: Jun. 4, 2019

(54) X-RAY DETECTING APPARATUS AND METHOD OF OPERATING THE SAME

(71) Applicant: SAMSUNG ELECTRONICS CO., LTD., Suwon-si (KR)

(72) Inventors: Sung-kyu Park, Uiwang-si (KR); Dae-yeong Jang, Suwon-si (KR); Key-jo Hong, Seoul (KR); Hee-cheol Kim, Seoul (KR); Jeong-geun Cho, Namyangju-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/142,702

(22) Filed: Apr. 29, 2016

(65) Prior Publication Data

US 2017/0209107 A1 Jul. 27, 2017

(30) Foreign Application Priority Data

Jan. 26, 2016 (KR) .................. 10-2016-0009400

(51) Int. Cl.
*A61B 6/00* (2006.01)
*G01T 1/24* (2006.01)
*A61B 6/03* (2006.01)

(52) U.S. Cl.
CPC .......... *A61B 6/4208* (2013.01); *A61B 6/4266* (2013.01); *A61B 6/54* (2013.01); *A61B 6/56* (2013.01); *G01T 1/244* (2013.01); *A61B 6/03* (2013.01); *A61B 6/032* (2013.01)

(58) Field of Classification Search
CPC .......... G01T 1/24; G01T 1/244; A61B 6/032; A61B 6/56; A61B 6/54; A61B 6/4208; A61B 6/4266
See application file for complete search history.

(56) References Cited

U.S. PATENT DOCUMENTS

| 5,924,979 | A | 7/1999 | Swedlow et al. |
| 6,486,808 | B1 * | 11/2002 | Seppi ................ H03M 1/129 |
| | | | 330/302 |
| 9,020,093 | B2 | 4/2015 | Kurochi et al. |
| 9,046,609 | B2 | 6/2015 | Chicchetti et al. |
| 2005/0207534 | A1 | 9/2005 | Petrick et al. |
| 2007/0206721 | A1 * | 9/2007 | Tkaczyk ................ A61B 6/032 |
| | | | 378/19 |
| 2009/0022276 | A1 * | 1/2009 | Ohara ................ A61B 6/00 |
| | | | 378/101 |
| 2011/0050403 | A1 | 3/2011 | Liu et al. |

(Continued)

FOREIGN PATENT DOCUMENTS

EP 1 857 048 A1 11/2007
JP 2012-177655 A 9/2012

(Continued)

OTHER PUBLICATIONS

Communication dated Apr. 27, 2017 issued by the Korean Intellectual Property Office in counterpart Korean Patent Application No. 10-2016-0009400.

(Continued)

*Primary Examiner* — Chih-Cheng Kao
(74) *Attorney, Agent, or Firm* — Sughrue Mion, PLLC

(57) ABSTRACT

Provided are an X-ray detecting apparatus which is capable of controlling an electric power supplied to an X-ray detector module while an X-ray tomography scanning is being performed, and a method for operating the X-ray detecting apparatus. The X-ray detecting apparatus includes an X-ray detector module which has a heat dissipation structure.

18 Claims, 13 Drawing Sheets

(56) References Cited

U.S. PATENT DOCUMENTS

| | | | |
|---|---|---|---|
| 2011/0133096 A1* | 6/2011 | Konkle | G01T 1/244 250/370.09 |
| 2012/0128127 A1* | 5/2012 | Chicchetti | A61B 6/4405 378/62 |
| 2013/0001429 A1 | 1/2013 | Dowaki et al. | |
| 2013/0039533 A1* | 2/2013 | Lacey | G01N 23/046 382/103 |
| 2013/0126742 A1* | 5/2013 | Hayun | A61B 6/542 250/366 |
| 2014/0064443 A1* | 3/2014 | Kato | A61B 6/4429 378/19 |
| 2016/0161616 A1* | 6/2016 | Nakayama | G01T 1/244 250/370.15 |

FOREIGN PATENT DOCUMENTS

| | | | | |
|---|---|---|---|---|
| JP | 2012177655 A * | 9/2012 | | |
| KR | 10-2012-0102660 A | 9/2012 | | |
| KR | 20120102660 A * | 9/2012 | | A61B 6/4405 |
| KR | 10-2013-0002947 A | 1/2013 | | |
| KR | 20130002947 A * | 1/2013 | | H04N 5/3745 |
| WO | WO 2012033029 A1 * | 3/2012 | | A61B 6/542 |
| WO | 2015025596 A1 | 2/2015 | | |
| WO | WO 2015025596 A1 * | 2/2015 | | G01T 1/244 |

OTHER PUBLICATIONS

Communication dated Apr. 28, 2017 issued by the European Patent Office in counterpart European Patent Application No. 16191758.8.

* cited by examiner

X-RAY DETECTING APPARATUS AND METHOD OF OPERATING THE SAME

CROSS-REFERENCE TO RELATED APPLICATION

This application claims priority from Korean Patent Application No. 10-2016-0009400, filed on Jan. 26, 2016, in the Korean Intellectual Property Office, the disclosure of which is incorporated herein by reference in its entirety.

BACKGROUND

1. Field

Exemplary embodiments relate to X-ray detecting apparatuses and methods for operating X-ray detecting apparatuses, and more particularly, to methods for controlling the supplying of electric power to an X-ray detector module included in an X-ray detecting apparatus while an X-ray scan is being performed, and X-ray detecting apparatuses configured to implement the methods.

2. Description of the Related Art

A medical imaging apparatus is an apparatus that is configured for acquiring images of internal structures of an object. A medical image apparatus is a noninvasive examination apparatus that shows the structural details, internal tissues, and fluid flow of a human body to a user. A user, such as a doctor, may diagnose a health state and a disease of a patient by using a medical image output by a medical image processing apparatus.

Examples of an apparatus for photographing an object by irradiating X-rays toward an object may include a computed tomography (CT) apparatus. A CT apparatus may provide cross-sectional images of an object, and express the internal structures (e.g., organs such as a kidney, a lung, and/or other body organs) of the object so as not to overlap each other, unlike general X-ray apparatuses. Thus, the CT apparatus is currently widely used for precisely diagnosing a disease.

In a medical imaging apparatus for photographing an object by irradiating an X-ray such as a CT apparatus, an X-ray detector is essentially provided for sensing an X-ray that has propagated through the object. In addition, the X-ray that has propagated through the object must be rapidly and precisely sensed in order to precisely reconstruct a medical image by using the sensed X-ray in subsequent processes.

Recently, as a slice photographed by a CT apparatus increases and pixels in the slice are reduced in size, the number of pixels tends to increase. Thus, a degree to which circuits included in an X-ray detecting apparatus are integrated has increased, and accordingly, a power consumption of the X-ray detecting apparatus and a heat generation amount from the X-ray detecting apparatus has also increased. Also, a standby time is necessary for stabilizing offset levels of an X-ray detector module and internal circuits, whereas an electric power is continuously supplied to the X-ray detector module during the standby time. Thus, heat generation from the X-ray detector module has further increased, and deterioration of the X-ray detecting apparatus has accelerated.

SUMMARY

Provided are methods for operating an X-ray detecting apparatus and X-ray detecting apparatuses capable of reducing a power consumed by the X-ray detecting apparatus including an X-ray detector module and preventing deterioration of the X-ray detecting apparatus, by controlling a power supplied to the X-ray detector module according to whether an X-ray tomography scan is performed.

Provided are X-ray detecting apparatuses which include an X-ray detector module that has a heat dissipation structure.

Additional aspects will be set forth in part in the description which follows and, in part, will be apparent from the description, or may be learned by practice of the presented exemplary embodiments.

According to an aspect of an exemplary embodiment, an X-ray detecting apparatus comprises at least one X-ray detector module configured to detect an X-ray irradiated from an X-ray generator toward an object in order to obtain X-ray data that relates to the object, wherein the at least one X-ray detector module comprises: a body that includes a metal material; a photodetector disposed at a side of the body and configured to receive the X-ray irradiated from the X-ray generator and to convert an X-ray signal into an electric signal; a first circuit board disposed on a first surface of the body; a first analog/digital converter (ADC) chip mounted on an upper surface of the first circuit board and configured to convert the electric signal into a digital signal; and a thermal pad interposed between the first surface of the body and an upper surface of the ADC chip.

For example, the first surface of the body and the upper surface of the first circuit board may face each other.

For example, the at least one X-ray detector module may further comprise: a second circuit board disposed on a second surface of the body, wherein the second surface is opposite to the first surface; a second ADC chip mounted on an upper surface of the second circuit board; and a thermal pad interposed between the second surface of the body and the second ADC chip.

For example, the photodetector may comprise: a scintillator configured to receive the X-ray irradiated from the X-ray generator, and to discharge the X-ray as photons of a visible frequency band; and a photodiode configured to convert the photons into an analog electric signal, wherein the photodiode is disposed at a side of the body and the scintillator is disposed on an upper surface of the photodiode.

For example, a plurality of the X-ray detector modules may be arranged in an array, and the X-ray detecting apparatus may further comprise a module connection frame which is configured for connecting the plurality of X-ray detector modules to each other.

For example, the body may comprise a first coupling joint that extends from the side of the body, where the photodetector is disposed, to protrude in a first direction, and a second coupling joint that extends from the side of the body to protrude in a second direction that is opposite to the first direction, and the module connection frame may comprise a first frame coupled to the first coupling joint and a second frame coupled to the second coupling joint.

For example, the plurality of X-ray detector modules may be installed in a gantry that is configured to rotate, and is disposed to face the X-ray generator that is installed in the gantry.

According to an aspect of another exemplary embodiment, an X-ray detecting apparatus comprises: at least one X-ray detector module configured to detect an X-ray irradiated from the X-ray generator toward an object, and to convert the detected X-ray into an electric signal based on a photograph protocol that relates to obtaining X-ray data about the object; a power supply configured to supply electric power to the at least one X-ray detector module; and a controller configured to receive a signal for starting an X-ray tomography scan with respect to the at least one X-ray detector module, and to control the power supply to supply the electric power to the at least one X-ray detector module when an X-ray tomography scan starts based on the received signal for starting the X-ray tomography scan and to terminate the supplying of the electric power to the at least one X-ray detector module when the X-ray tomography scan is completed.

For example, the controller may control the power supply to terminate the supplying of the electric power to the at least one X-ray detector module, without having received the signal for starting the X-ray tomography scan.

For example, the controller may be further configured to recognize at least one change in an external environment of the at least one X-ray detector module, and to control the power supply to supply the electric power to the at least one X-ray detector module or to terminate the supplying of the electric power to the at least one X-ray detector module based on the recognized at least one change in the external environment of the at least one X-ray detector module.

For example, the at least one X-ray detector module may be further configured to acquire an X-ray raw data image that relates to the object, and the controller may be further configured determine that the X-ray tomography scan is completed by analyzing header information included in the X-ray raw data image and to control the power supply to terminate the supplying of the electric power to the at least one X-ray detector module based on the determination.

For example, the X-ray detecting apparatus may further comprising a storage configured for storing a setting parameter value that relates to a scan of the at least one X-ray detector module, wherein the stored setting parameter value comprises information that relates to at least one from among an offset calibration of the at least one X-ray detector module and a feedback capacitor included in the at least one X-ray detector module.

For example, the at least one X-ray detector module may further comprise a detector module controller configured for correcting at least one from among an offset value of the at least one X-ray detector module and a feedback capacitor value, based on the stored setting parameter value.

For example, the detector module controller may receive the setting parameter value of the at least one X-ray detector module from the storage, when an X-ray tomography scan starts based on a reception of a signal for starting the X-ray tomography scan.

According to an aspect of another exemplary embodiment, a method for operating an X-ray detecting apparatus that comprises at least one X-ray detector module configured for detecting an X-ray irradiated from an X-ray generator toward an object and for obtaining X-ray data that relates to the object is provided. The method comprises: receiving a signal for starting an X-ray tomography scan; supplying electric power to the at least one X-ray detector module; detecting an X-ray irradiated toward the object based on a photograph protocol that relates to obtaining X-ray data of the object; and terminating the supplying of the electric power to the at least one X-ray detector module.

For example, the method may further comprise terminating the supplying of the electric power to the at least one X-ray detector module, before receiving the signal for starting the X-ray tomography scan.

For example, the receiving the signal for starting the X-ray tomography scan may comprise: recognizing at least one change in an external environment of the at least one X-ray detector module; and determining whether to initiate or to terminate the supplying of the electric power to the at least one X-ray detector module based on the recognized at least one change in the external environment.

For example, the obtaining of the X-ray data may comprise obtaining X-ray raw data that relates to the object, and the terminating the supplying of the electric power to the at least one X-ray detector module may comprise: determining that the X-ray tomography scan is completed by analyzing header information of the X-ray raw data; and terminating the supplying of the electric power to the at least one X-ray detector module based on the determination.

For example, the method may further comprising receiving a setting parameter value that relates to a scan of the at least one X-ray detector module, after the supplying of the electric power to the at least one X-ray detector module.

For example, the setting parameter value may comprise information that relates to at least one from among an offset calibration of the at least one X-ray detector module and a feedback capacitor included in the at least one X-ray detector module, and the method may further comprise correcting at least one from among an offset value of the at least one X-ray detector module and a feedback capacitor value, based on the setting parameter value.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
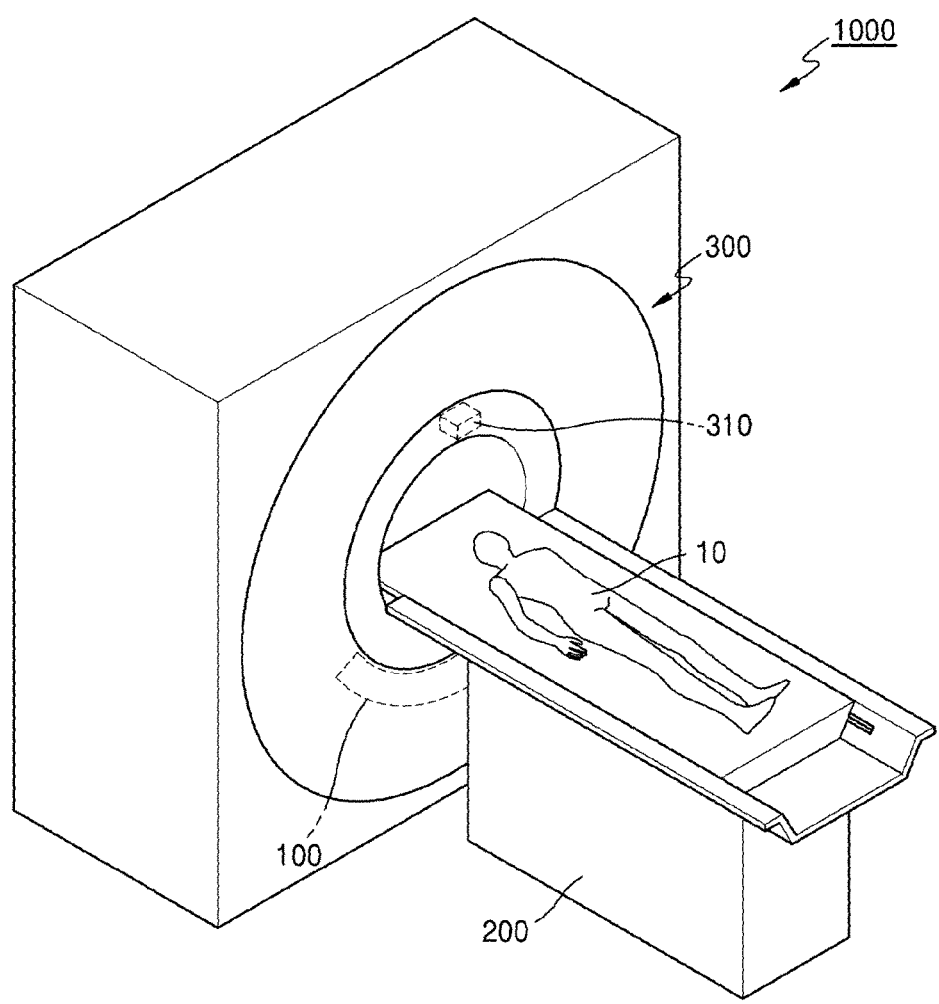
FIG. 1 is a schematic diagram of a general computed tomography (CT) apparatus.

Advantages and features of one or more exemplary embodiments and methods of accomplishing the same may be understood more readily by reference to the following detailed description of the exemplary embodiments and the accompanying drawings. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to persons of ordinary skill in the art, and the present inventive concept will only be defined by the appended claims. Like reference numerals refer to like elements throughout the specification.

Hereinafter, the terms used in the specification will be briefly defined, and the exemplary embodiments will be described in detail.

The terms used in this specification are those general terms currently widely used in the art in consideration of functions regarding the exemplary embodiments, but the terms may vary according to the intention of those of ordinary skill in the art, precedents, or new technology in the art. In addition, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. Further, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to exemplary embodiments, examples of which are illustrated in the accompanying drawings. In this regard, the present exemplary embodiments may have different forms and should not be construed as being limited to the descriptions set forth herein. In the following description, well-known functions or constructions are not described in detail so as not to obscure the exemplary embodiments with unnecessary detail.

Throughout the specification, an "image" may mean multi-dimensional data formed of discrete image elements, e.g., pixels in a two-dimensional (2D) image and voxels in a three-dimensional (3D) image. For example, the image may include a medical image of an object which is captured by a computed tomography (CT) imaging apparatus.

Throughout the specification, a "CT image" may mean an image generated by synthesizing a plurality of X-ray images that are obtained by photographing an object while a CT imaging apparatus rotates around at least one axis with respect to the object.

Throughout the specification, an "object" may be a human, an animal, or a portion of a human or animal. For example, the object may be an organ (e.g., the liver, heart, womb, brain, breast, or abdomen), a blood vessel, or a combination thereof. In addition, the object may be a phantom. The term "phantom" refers to a material having a density, an effective atomic number, and a volume that are approximately the same as those of an organism. For example, the phantom may be a spherical phantom that has properties which are similar to the physical body.

Throughout the specification, a "user" may be, but is not limited to, a medical expert including a medical doctor, a nurse, a medical laboratory technologist, a medial image expert, and/or a technician who repairs a medical apparatus.

Since a CT imaging apparatus is capable of providing a cross-sectional image of an object, the CT imaging apparatus may distinctively express an inner structure, e.g., an organ such as a kidney or a lung of the object, as compared with a general X-ray imaging apparatus.

The CT imaging apparatus may obtain a plurality of pieces of image data, each of which has a thickness not more than 2 mm, several tens to several hundred times per second, and then may process the plurality of pieces of image data, so that the CT imaging apparatus may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method for displaying only voxels which have a predetermined Hounsfield Units (HU) value.

Maximum intensity projection (MIP)/minimum intensity projection (MinIP)—a 3D imaging method for displaying only voxels which have the greatest or smallest HU value from among voxels that construct an image.

Volume rendering (VR)—an imaging method for adjusting a color and transmittance of voxels that constitute an image, according to areas of interest.

Virtual endoscopy—a method that facilitates endoscopy observation in a 3D image that is reconstructed by using the VR method or the SSD method.

Multi-planar reformation (MPR)—a method for reconstructing an image into a different cross-sectional image. A user may reconstruct an image in any desired direction.

Editing—a method for editing adjacent voxels so as to enable a user to easily observe an area of interest in volume rendering.

Voxel of interest (VOI)—a method for displaying only a selected area in volume rendering.

A CT imaging apparatus 1000 according to an exemplary embodiment will now be described with reference to FIGS. 1 and 2. The CT imaging apparatus 1000 may include any of various types of devices.

FIG. 1 is a schematic diagram of a computed tomography (CT) system 1000. Referring to FIG. 1, the CT system 1000 may include an X-ray detecting apparatus 100, a table 200, a gantry 300, and an X-ray generator 310.

An object 10 may be positioned on the table 200.

The gantry 300 may include the X-ray detecting apparatus 100 and the X-ray generator 310.

The table 200 may be configured to move in a predetermined direction (e.g., at least one of upward, downward, rightward, and leftward directions) during a CT imaging procedure. Further, the table 200 may be configured to tilt or rotate by a predetermined angle in a predetermined direction.

The gantry 300 may also be configured to tilt by a predetermined angle in a predetermined direction.

Figure 2:
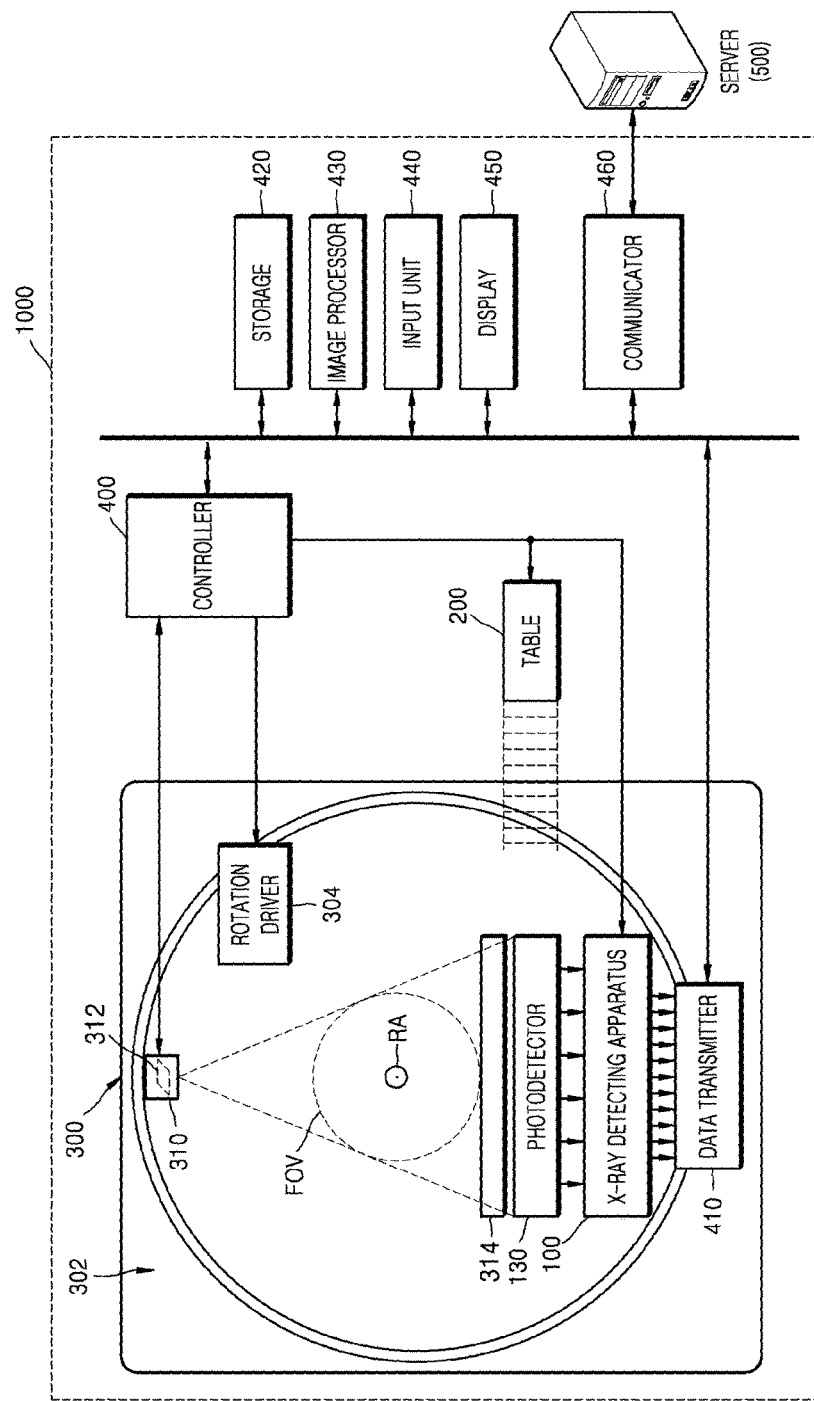
FIG. 2 is a diagram of a structure in a CT system, according to an exemplary embodiment.

FIG. 2 is a block diagram illustrating a structure of the CT imaging apparatus 1000.

The CT system 1000 according to the exemplary embodiment may include the X-ray detecting apparatus 100, the table 200, the gantry 300, a controller 400, a storage 420, an image processor 430, an input unit (also referred to herein as an "input device") 440, a display 450, and a communicator 460.

As described above, the object 10 may be positioned on the table 200. In the present exemplary embodiment, the table 200 may move in a predetermined direction (e.g., at least one of upward, downward, rightward, and leftward directions), and movement of the table 105 may be controlled by the controller 400.

The gantry 300 according to the exemplary embodiment may include a rotating frame 302, the X-ray generator 310, a rotating driver 304, and a data transmitter 410. In an exemplary embodiment, an photodetector 130 and the X-ray detecting apparatus 100 may be provided at a side of the gantry 300.

The gantry 300 may include the rotating frame 302 that has a loop shape which is capable of rotating with respect to a predetermined rotation axis RA. Alternatively, the rotating frame 302 may have a disc shape.

The rotating frame 302 may include the X-ray generator 310 and the X-ray detector apparatus 100 that are arranged to face each other so as to have predetermined fields of view FOV. The rotating frame 302 may also include an anti-scatter grid 314. The anti-scatter grid 314 may be positioned between the X-ray generator 310 and the X-ray detector apparatus 100.

In a medical imaging system, X-ray radiation that reaches a detector (or a photosensitive film) includes not only attenuated primary radiation that forms a valuable image, but also scattered radiation that deteriorates the quality of an image. In order to facilitate propagation of most of the primary radiation and to attenuate the scattered radiation, the anti-scatter grid 314 may be positioned between a patient and the detector (or the photosensitive film).

For example, the anti-scatter grid 314 may be formed by alternately stacking lead foil strips and an interspace material such as a solid polymer material, solid polymer, or a fiber composite material. However, formation of the anti-scatter grid 314 is not limited thereto.

The rotating frame 302 may receive a driving signal from the rotation driver 304 and may cause the X-ray generator 310 and the X-ray detector apparatus 100 to rotate at a predetermined rotation speed. The rotating frame 302 may receive the driving signal and power from the rotation driver 304 while the rotating frame 302 contacts the rotation driver 304 via a slip ring (not shown). Further, the rotating frame 302 may receive the driving signal and power from the rotation driver 304 via wireless communication.

The X-ray generator 310 may receive a voltage and current from a power distribution unit (PDU) (also referred to herein as a "power distributor") (not shown) via a slip ring (not shown) and then a high voltage generating unit (also referred to herein as a "high voltage generator") (not shown), and may generate and emit an X-ray. When the high voltage generating unit applies a predetermined voltage (hereinafter, referred to as a tube voltage) to the X-ray generator 310, the X-ray generator 310 may generate X-rays which have a plurality of energy spectra that correspond to the tube voltage.

The X-ray generated by the X-ray generator 310 may be emitted in a predetermined form due to a collimator 312.

The X-ray detector apparatus 100 may be positioned to face the X-ray generator 310. Each of the plurality of X-ray detecting devices may establish one channel but one or more exemplary embodiments are not limited thereto.

The photodetector 130 may detect the X-ray that is generated by the X-ray generator 310 and that has propagated through the object 10, and may generate an electrical signal that corresponds to an intensity of the detected X-ray.

The photodetector 130 may include an indirect-type X-ray detector configured for detecting radiation after converting the radiation into light, and a direct-type X-ray detector configured for detecting radiation after directly converting the radiation into electrical charges. The indirect type photodetector 130 may use a scintillator. Further, the direct-type photodetector 130 may use a photon counting detector. The X-ray detecting apparatus 100 may be connected to the photodetector 130. An electric signal generated by the photodetector 130 may be collected by the X-ray detecting apparatus 100. The electric signal generated by the photodetector 130 may be collected by the X-ray detecting apparatus 100 via wired or wireless communication. In FIG. 2, the photodetector 130 and the X-ray detecting apparatus 100 are separate from each other, but the exemplary embodiments are not limited thereto, that is, the photodetector 130 may be included in the X-ray detecting apparatus 100.

According to a slice thickness or the number of slices, only some of a plurality of pieces of data collected by the X-ray detector apparatus 100 may be provided to the image processor 430 via the data transmitter 410, or the image processor 430 may select only some of the plurality of pieces of data.

Such a digital signal may be provided to the image processor 430 via the data transmitter 410. The digital signal may be provided to the image processor 430 by wire or wirelessly.

The controller 400 may control an operation of each of the elements in the CT imaging apparatus 1000. For example, the controller 400 may control overall operations of the X-ray detecting apparatus 100, the table 200, the rotation driver 302, a collimator 312, the storage 420, the image processor 430, the input unit 440, the display 450, and the communicator 460.

The image processor 430 receives data acquired by the X-ray detecting apparatus 100 (e.g., raw data before being processed) via the data transmitter 410, and performs a pre-processing of the data.

The pre-processing may include, for example, a process of correcting a sensitivity irregularity between channels and a process of correcting signal loss due to a rapid decrease in signal strength or due to the presence of an X-ray absorbing material such as metal.

Data output from the image processor 430 may be referred to as raw data or projection data. The projection data may be stored in the storage 420 with imaging conditions (e.g., the tube voltage, an imaging angle, etc.) during the acquisition of data.

The projection data may include a group of data values that correspond to the intensity of the X-ray that has propagated through the object 10. For convenience of description, a group of a plurality of pieces of projection data that are simultaneously obtained from all channels at the same imaging angle is referred to hereinafter as a projection data set.

The storage 420 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processor 430 may reconstruct a cross-sectional image of the object 10 by using the acquired projection data set. The cross-sectional image may be a 3D image. In particular, the image processor 430 may reconstruct a 3D image of the object 10 by using a cone beam reconstruction method or the like, based on the acquired projection data set.

The input unit 440 may receive an external input with respect to an X-ray tomography imaging condition, an image processing condition, and/or the like. For example, the X-ray tomography imaging condition may include any one or more of tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, and/or the like. Further, the image processing condition may include any one or more of a resolution of an image, an attenuation coefficient setting for the image, a setting for an image combining ratio, and/or the like.

The input unit 440 may include a device that is configured for receiving a predetermined input from an external source. For example, the input unit 440 may include any one or more of a microphone, a keyboard, a mouse, a joystick, a touch pad, a touch pen, a voice recognition device, a gesture recognition device, and/or the like.

The display 450 may be configured to display an X-ray image reconstructed by the image processor 430.

Exchanges of data, power, or the like between the aforementioned elements may be performed by using at least one of wired communication, wireless communication, and optical communication.

The communicator 460 may perform communication with an external device, an external medical apparatus, and/or any other suitable device via a server 500 or the like. The communication will now be described with reference to FIG. 3.

Figure 3:
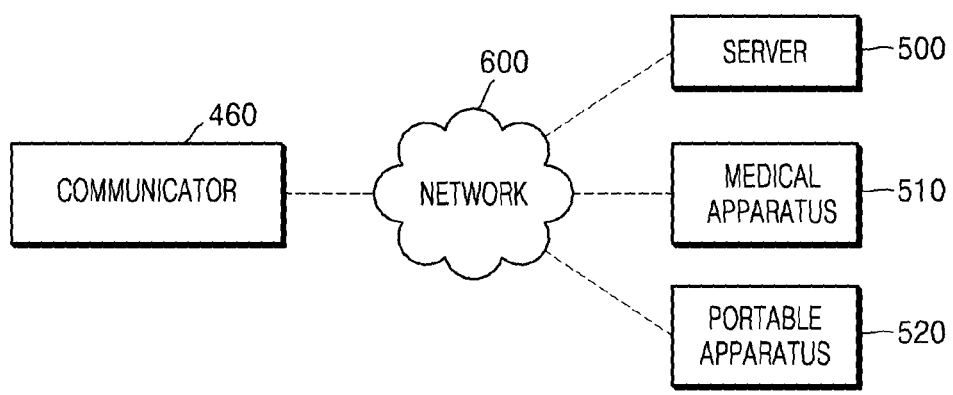
FIG. 3 is a diagram of a communicator in a CT system, according to an exemplary embodiment.

FIG. 3 is a diagram of the communicator 460 of the CT system 1000.

The communicator 460 may be wiredly or wirelessly connected to a network 600 and therefore may perform communication with the server 500, a medical apparatus 510, and/or a portable device 520. The communicator 460 may exchange data with a hospital server or another medical apparatus in a hospital, which may be connected thereto via a picture archiving and communication system (PACS).

Further, the communicator 460 may perform data communication with the portable device 520 or the like, according to the digital imaging and communications in medicine (DICOM) standard.

The communicator 460 may transmit and receive data related to diagnosing the object 10, via the network 600. Further, the communicator 460 may transmit and receive a medical image obtained from the medical apparatus 510 such as a magnetic resonance imaging (MRI) apparatus, an X-ray apparatus, or the like.

Furthermore, the communicator 460 may receive a diagnosis history or a medical treatment schedule that relates to a patient from the server 500, and may use the diagnosis history or the medical treatment schedule to diagnose the patient. In addition, the communicator 460 may perform data communication not only with the server 500 or the medical apparatus 510 in a hospital, but also with the portable device 520 of a user or patient.

Still further, the communicator 460 may transmit information about a device error, information about a quality control status, and/or the like to a system manager or a service manager via the network 600, and may receive a feedback regarding the transmitted information from the system manager or service manager.

Figure 4:
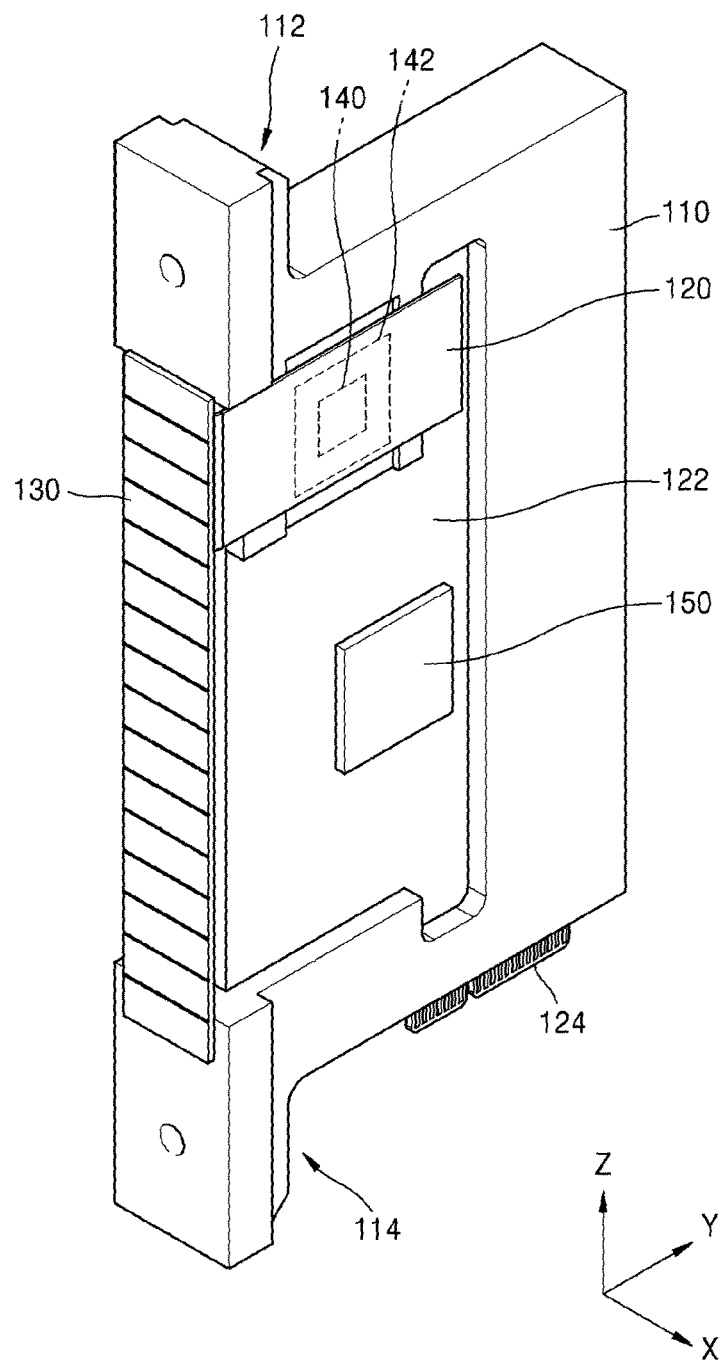
FIG. 4 is a perspective view of an X-ray detector module, according to an exemplary embodiment.

FIG. 4 is a perspective view of an X-ray detector module 100-1, according to an exemplary embodiment.

Referring to FIG. 4, the X-ray detector module 100-1 may include a body 110, a first circuit board 120, a photodetector 130, an analog/digital converter (ADC) chip 140, and a thermal pad 142. In an exemplary embodiment, the X-ray detector module 100-1 may further include a second circuit board 122, a connection member 124, and a detector module controller 150.

The body 110 may have a hexahedral shape having a predetermined thickness. The first circuit board 120, the second circuit board 122, the connection member 124, the photodetector 130, the ADC chip 140, the thermal pad 142, and the detector module controller 150 may be mounted or disposed on the body 110.

The first circuit board 120 may be disposed on a side surface of the body 110. The second circuit board 122 may be disposed at the same side surface upon which the first circuit board 120 is disposed. A portion of the body 110, on which the second circuit board 122 is disposed, has a height in a first direction (X-direction) that may be less than a height of a portion on which the first circuit board 120 is disposed, in the first direction (X-direction). In particular, the side surface of the body 110, on which the second circuit board 122 is disposed, may be engraved in the first direction (X-direction).

The photodetector 130 may be disposed on a side surface that is adjacent to the side surface of the body 110, on which the first and second circuit boards 120 and 122 are disposed. A first coupling portion 112 that extends so as to protrude in a third direction (Z-direction) and a second coupling portion 114 that extends so as to protrude opposite to the direction in which the first coupling portion 112 extends may be formed on the side surface of the body 110, on which the photodetector 130 is disposed.

The body 110 may include a metal material that has high thermal conductivity. The body 110 may include, for example, at least one from among aluminum (Al), copper (Cu), magnesium (Mg), iron (Fe), silver (Ag), platinum (Pt), gold (Au), and an alloy thereof, but is not limited thereto. In an exemplary embodiment, the body 110 may include Al.

The first circuit board 120 is a support board on which the ADC chip 140 is mounted, and may be formed on a basis of at least one selected from among a printed circuit board (PCB), a ceramic substrate, an organic substrate, an interposer substrate, and a package substrate. The ADC chip 140 is mounted on an upper surface of the first circuit board 120, and the upper surface of the first circuit board 120 may disposed so as to face a side surface of the body 110. A structure that is configured for disposing the first circuit board 120 on the body 110 will be described below with reference to FIGS. 5A and 5B.

Similarly as the first circuit board 120, the second circuit board 122 may be formed on a basis of at least one selected from among a PCB, a ceramic substrate, an organic substrate, an interposer substrate, and a package substrate.

The second circuit board 122 may include a connection member 124 that may be connected to an external device, e.g., at least one of the controller 400, the storage 420, the image processor 430, the input unit 440, the display 450, and the communicator 460 (see FIG. 2). In addition, the connection member 124 may have a function of mounting the X-ray detector module 100-1 on an external system substrate or a main board. In an exemplary embodiment, the X-ray detector module 100-1 is connected to a power supply unit at the outside via the connection member 124 in order to receive the power supply.

The photodetector 130 may be disposed at a side of the body 110. A plurality of photodetectors 130 that are arranged in an array may be provided. The photodetectors 130 receive the X-ray generated by the X-ray generator 310 (see FIGS. 1 and 2), and may convert an X-ray signal into an electric signal.

The ADC chip 140 may be mounted on the upper surface of the first circuit board 120. The ADC chip 140 may convert an analog signal that has been converted by the photodetector 130 into a digital signal. The ADC chip 140 may include at least one from among a central processing unit (CPU), a microprocessor, and a graphic processing unit (GPU) that has a computational function of converting an analog signal into a digital signal.

The thermal pad 142 may be interposed between an upper surface of the ADC chip 140 and a side surface of the body 110. The thermal pad 142 may transfer heat dissipated from the ADC chip 140 to the body 110. The thermal pad 142 may include a curing material that has a relatively high thermal conductivity. For example, the thermal pad 142 may include a mixture of at least one binder and a harder, wherein the at least one binder is selected from among a silicon resin, a polyurethane resin, a polybutadien resin, polyisoprene resin, a natural rubber resin, a polyvinyl chloride resin, a polyisoprenepolyethylene resin, a polypropylen resin, a polyvinylidene chloride resin, and a plasticized resin thereof. However, the material included in the thermal pad 142 is not limited to the above examples.

The detector module controller 150 may be mounted on the second circuit board 122. The detector module controller 150 may control overall operations of the photodetector 130 and the ADC chip 140. The detector module controller 150 may be implemented as, but is not limited to, a hardware component such as a field programmable gate array (FPGA) or an application specific integrated circuit (ASIC).

In FIG. 4, one ADC chip 140 and one detector module controller 150 are included for convenience of description, but the X-ray detector module 100-1 may include a plurality of ADC chips 140 and a plurality of detector module controllers 150. In particular, a photodiode 134 (see descriptions of FIGS. 5A and 5B below) included in the photodetector 130 and the ADC chip 140 are connected to each other in one-to-one correspondence. As the number of pixels in a CT image has increased recently, multi-channel ADC chips 140 and detector module controllers 150 have become necessary, and accordingly, heat generated by the X-ray detector module 100-1 increases. Further, because the X-ray detector module 100-1 generally performs high capacity and high speed electrical operations, as compared with the components in the CT system 1000 (see FIGS. 1 and 2), the X-ray detector module 100-1 consumes a relatively large amount of electric power.

In the X-ray detector module 100-1 shown in FIG. 4, the ADC chip 140 that generates a relatively large amount of heat is mounted on the upper surface of the first circuit board 120, the first circuit board 120 is disposed so that an upper surface of the first circuit board 120 faces a side surface of the body 110, and the thermal pad 142 is interposed between the ADC chip 140 and the body 110 so that the heat generated by the ADC chip 140 may be effectively discharged toward the body 110. In addition, according to the X-ray detector module 100-1 of the exemplary embodiment, the body 110 includes a metal material that has a relatively high thermal conductivity so that the heat generated by the detector module controller 150, as well as the heat generated by the ADC chip 140, may be effectively discharged.

Figure 5A:
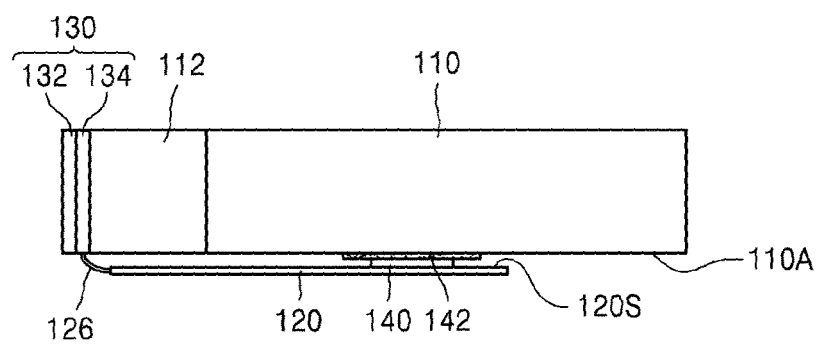
FIGS. 5A and 5B are plan views of an X-ray detector module, according to an exemplary embodiment.
Figure 5A:
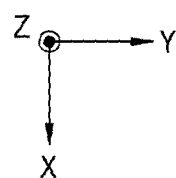
Figure 5B:
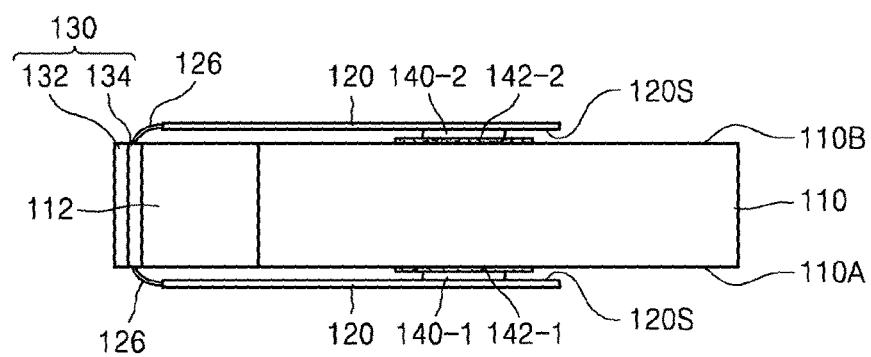
Figure 5B:
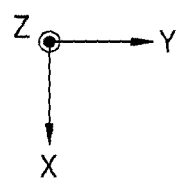

FIGS. 5A and 5B are plan views of the X-ray detector module 100-1, according to an exemplary embodiment.

Referring to FIG. 5A, the X-ray detector module 100-1 may include the body 110, the first circuit board 120, a wiring 126, the photodetector 130, the ADC chip 140, and the thermal pad 142.

The ADC chip 140 is mounted on an upper surface 120S of the first circuit board 120, and the thermal pad 142 may be interposed between the ADC chip 140 and a first surface 110A of the body 110. The upper surface 120S of the first circuit board 120 may face the first surface 110A of the body 110.

In FIG. 5A, the first circuit board 120 and the first surface 110A of the body 110 are spaced apart from each other by a predetermined distance, but the distance is exaggerated for clarity of description. The first circuit board 120 and the body 110 are not limited to the example illustrated in FIG. 5A.

The wiring 126 may electrically and/or physically connect the first circuit board 120 to the photodetector 130. In an exemplary embodiment, the wiring 126 may electrically connect the photodiode 134 to the first circuit board 120. In an exemplary embodiment, the wiring 126 is arranged to be in direct physical contact with the first coupling portion 112, and the photodiode 134 may cover an entire upper portion of the wiring 126. The wiring 126 may include a metal material that has an electric conductivity. The wiring 126 may include, for example, at least one from among aluminum (Al), gold (Au), beryllium (Be), bismuth (Bi), cobalt (Co), copper (Cu), hafnium (Hf), indium (In), manganese (Mn), molybdenum (Mo), nickel (Ni), lead (Pb), palldium (Pd), platinum (Pt), rhodium (Rh), rhenium (Re), ruthenium (Ru), tantalium (Ta), tellurium (Te), titanium (Ti), tungsten (W), zinc (Zn), and zirconium (Zr), but the exemplary embodiment is not limited thereto.

The X-ray detector module 100-1 may further include an elastic gasket unit that surrounds the wiring 126 and has an electric insulating property.

The photodetector 130 may include the photodiode 134 disposed in contact with a side of the first coupling portion 112, and a scintillator 132 which contacts the photodiode 134 while covering the photodiode 134.

The scintillator 132 reacts with the X-ray that is irradiated by the X-ray generator 310 (see FIGS. 1 and 2) toward the object 10 (see FIG. 1) so as to discharge photons that have a wavelength of a visible frequency band.

The photodiode 134 receives the photons discharged from the scintillator 132, and converts the photons into electric signals. The photodiode 134 converts the photons into analog electric signals, and transmits the analog electric signals to the ADC chip 140.

Referring to FIG. 5B, the X-ray detector module 100-1 may include two first circuit boards 120, one of which is disposed on the first surface 110A of the body 110, and the other of which is disposed on a second surface 110B of the body which is opposite to the first surface 110A. The X-ray detector module 100-1 of FIG. 5B is the same as the X-ray detector module 100-1 of FIG. 5A, except two first circuit boards 120, first and second ADC chips 140-1 and 140-2 respectively mounted on the two first circuit boards 120, a thermal pad 142-1 interposed between the first surface 110A of the body 110 and the first ADC chip 140-1, and a thermal pad 142-2 interposed between the second surface 110B of the body 110 and the second ADC chip 140-2. Therefore, detailed descriptions about the same elements as those of FIG. 5A will be omitted hereinafter. The first and second ADC chips 140-1 and 140-2 are terminologies used to emphasize structural differences of the X-ray detector module 100-1 of FIG. 5B from the X-ray detector module 100-1 of FIG. 5A, but there is no requirement that the X-ray detector module 100-1 only includes two ADC chips 140-1 and 140-2.

The first circuit boards 120 may be disposed on opposite side surfaces of the body 110 in a first direction (X-direction). In more detail, the first circuit boards 120 are spaced a predetermined distance apart from the first surface 110A of the body 110, and also spaced a predetermined distance apart from the second surface 110B of the body 110. The upper surfaces 120S of the first circuit boards 120 may respectively face the first surface 110A and the second surface 110B of the body 110. The first and second ADC chips 140-1 and 140-2 may be respectively mounted on the two first circuit boards 120. The thermal pads 142-1 and 142-2 may be respectively interposed between the first surface 110A of the body 110 and the first ADC chip 140-1 and between the second surface 110B of the body 110 and the second ADC chip 140-2.

The first circuit board 120 disposed on the first surface 110A of the body 110 and the first circuit board 120 disposed on the second surface 110B of the body 110 may be electrically and/or physically connected to each other via the wiring 126. As shown in FIG. 5B, the wiring 126 may connect opposite side surfaces of the photodiode 134 to each other, but the exemplary embodiment is not limited thereto.

Figure 6A:
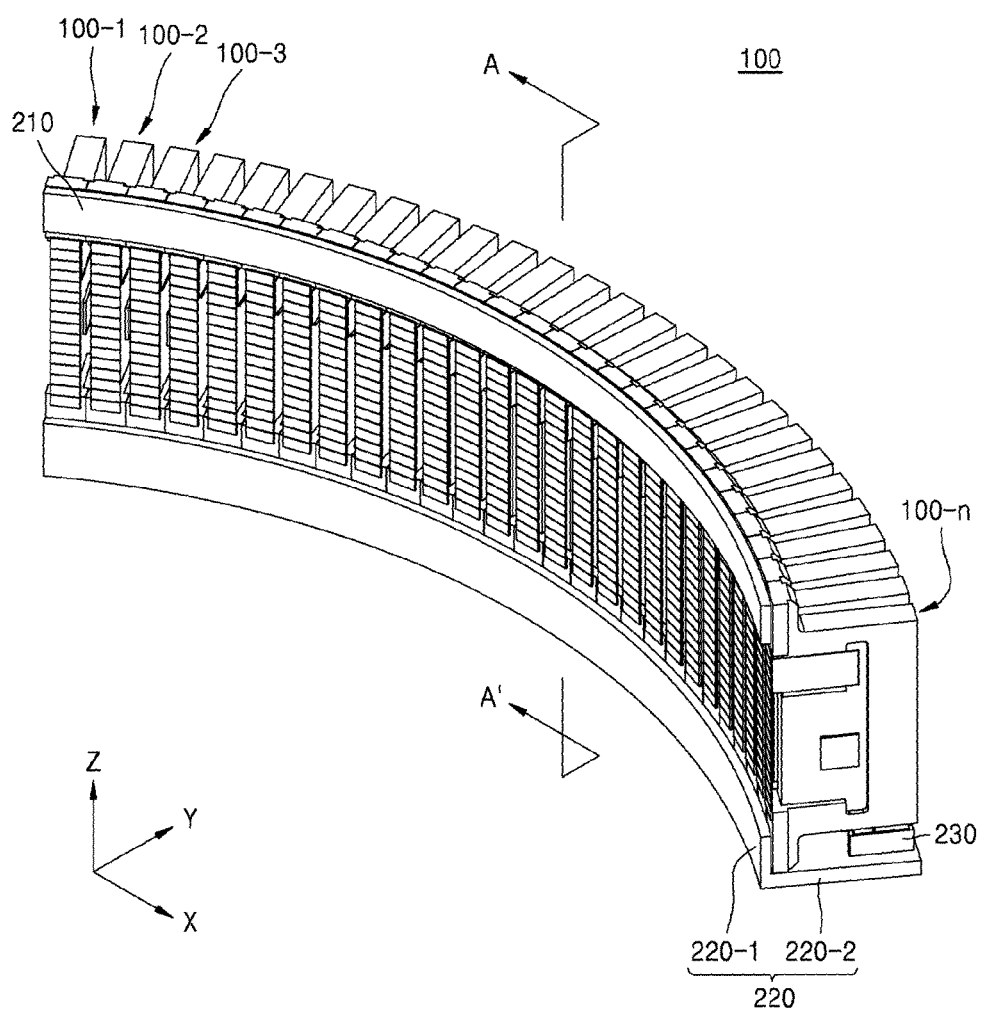
FIG. 6A is a perspective view of an X-ray detecting apparatus, according to an exemplary embodiment.

FIG. 6A is a perspective view of the X-ray detecting apparatus 100, according to an exemplary embodiment.

Referring to FIG. 6A, the X-ray detecting apparatus 100 may include a plurality of X-ray detector modules 100-1, 100-2, 100-3, . . . 100-n. The X-ray detecting apparatus 100 may include the plurality of X-ray detector modules 100-1 to 100-n that are arranged and connected to each other as an array. The X-ray detecting apparatus 100 includes the X-ray detector modules 100-1 to 100-n that are arranged so as to form an arc that subtends a predetermined central angle.

The X-ray detecting apparatus 100 may include first and second module connection frames 210 and 220 which connect the plurality of X-ray detector modules 100-1 to 100-n to each other. The module connection frames 210 and 220 include a first module connection frame 210 coupled to the first coupling joint 112 (see FIG. 6B) in each of the plurality of X-ray detector modules 100-1 to 100-n, and a second module connection frame 220 coupled to the second coupling joint 114 (see FIG. 6B) in each of the plurality of X-ray detector modules 100-1 to 100-n. The first module connection frame 210 and the second module connection frame 220 may be spaced apart from each other along a third direction (Z-direction). The second module connection frame 220 may include a connection portion 220-1 that connects to the plurality of X-ray detector modules 100-1 to 100-n, and a support portion 220-2 that extends in the first direction (X-direction) and has a connection member 230 mounted thereon.

The first and second module connection frames 210 and 220 may include a metal material that has a relatively high thermal conductivity. The first and second module connection frames 210 and 220 may include, for example, at least one of Al, Cu, Mg, Fe, Ag, Pt, Au, and an alloy thereof, but are not limited thereto. In an exemplary embodiment, the first and second module connection frames 210 and 220 may include the same metal material as that of the body 110.

Figure 6B:
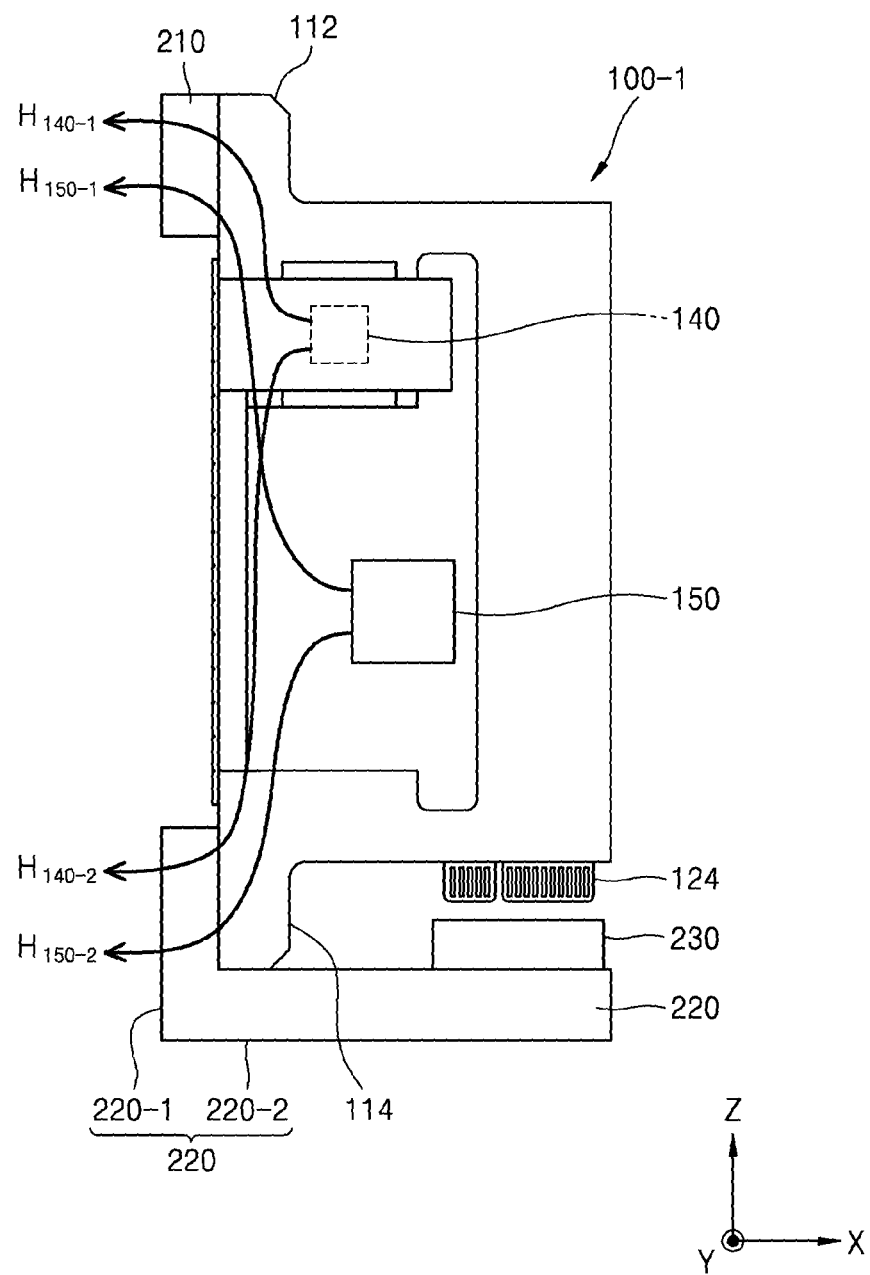
FIG. 6B is a cross-sectional view of an X-ray detecting apparatus, according to an exemplary embodiment.

FIG. 6B is a cross-sectional view of the X-ray detecting apparatus 100 taken along a line A-A' of FIG. 6A.

Referring to FIG. 6B, the X-ray detector module 100-1 may be connected to the first module connection frame 210 and the second module connection frame 220. In particular, the first coupling joint 112 of the X-ray detector module 100-1 may be coupled to the first module connection frame 210, and the second coupling joint 114 of the X-ray detector module 100-1 may be coupled to the second module connection frame 220. Although not shown in FIG. 6B, the first coupling joint 112 may be coupled to the first module connection frame 210 via a coupling member, such as, for example, a screw. Likewise, the second coupling portion 114 may be coupled to the second module connection frame 220 via a coupling member such as a screw.

The connection member 124 may be electrically and/or physically connected to the connection member 230. The X-ray detector module 100-1 may be connected to an external device, an external system substrate, or a main board, and may transmit/receive electric signals via the connection member 124 and the connection member 230. In an exemplary embodiment, the X-ray detector module 100-1 may be connected to a power supply 170 (see FIG. 8) in order to receive power supply via the connection member 124 and the connection member 230.

Heat generated by the ADC chip 140 and the detector module controller 150 may be discharged to the first module connection frame 210 and the second module connection frame 220 via the first coupling joint 112 and the second coupling joint 114. In detail, the heat generating from the ADC chip 140 may be discharged to the outside through a passage $H_{140-1}$ that proceeds toward the first module connection frame 210 through the first coupling joint 112, and a passage $H_{140-2}$ that proceeds toward the second module connection frame 220 through the second coupling joint 114. Heat generated by the detector module controller 150 may be discharged to the outside through a passage $H_{150-1}$ that proceeds toward the first module connection frame 210 through the first coupling joint 112, and a passage $H_{150-2}$ that proceeds toward the second module connection frame 220 through the second coupling joint 114.

The heat generated by the X-ray detector module 100-1 of FIG. 6B may be discharged to the outside through the first module connection frame 210 and the second module connection frame 220, and accordingly, efficiency in heat dissipation may be improved. In particular, since the body 110 and the first and second module connection frames 210 and 220 all include the metal material that has a relatively high thermal conductivity, the heat may be discharged sufficiently to the outside, and an undesirable rise in a temperature of the X-ray detector module 100-1 may be prevented.

Figure 7A:
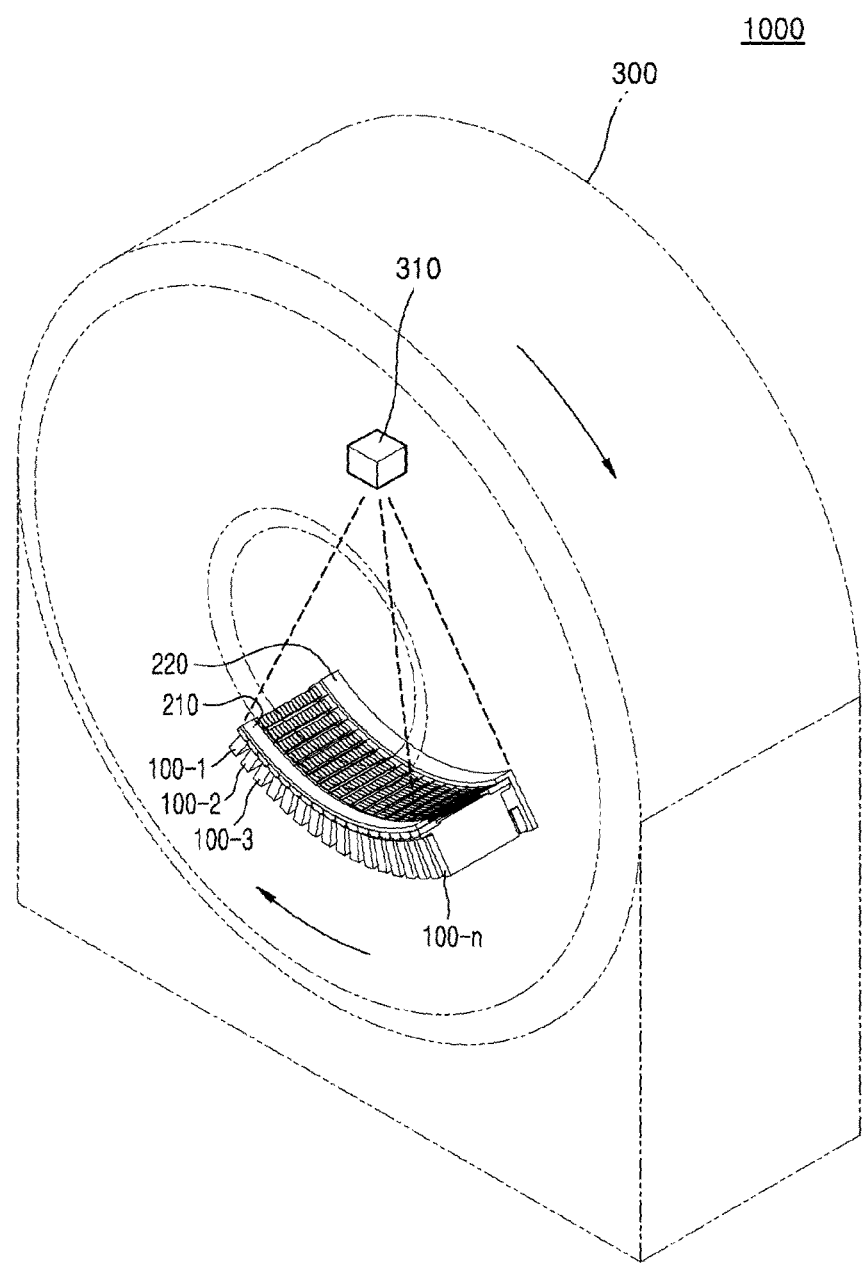
FIG. 7A is a diagram of a CT system, according to an exemplary embodiment.

FIG. 7A is a diagram of the CT system 1000, according to an exemplary embodiment.

Referring to FIG. 7A, the CT system 1000 may include the plurality of X-ray detector modules 100-1 to 100-*n*, the first and second module connection frames 210 and 220, the gantry 300, and the X-ray generator 310.

The gantry 300 may include a rotary frame that is configured to pivot about a predetermined rotary axis. The rotary frame may be formed as a disc.

The plurality of X-ray detector modules 100-1 to 100-*n* are connected to each other via the first and second module connection frames 210 and 220, and may be placed on a side in the gantry 300. The second frame 220 may be connected to a side of the gantry 300. In an exemplary embodiment, the plurality of X-ray detector modules 100-1 to 100-*n* may be directly connected to the gantry 300 without being coupled to the second module connection frame 220.

The X-ray generator 310 may be located in the gantry 300 so as to face the plurality of X-ray detector modules 100-1 to 100-*n*. The plurality of X-ray detector modules 100-1 to 100-*n* may detect an X-ray irradiated from the X-ray generator 310.

According to the CT system 1000 of the present exemplary embodiment, the plurality of X-ray detector modules 100-1 to 100-*n* are connected to each other via the first and second module connection frames 210 and 220, and installed in the gantry 300 that rotates so that the heat generated by the plurality of X-ray detector modules 100-1 to 100-*n* may be effectively discharged to an outside of the gantry 300. In particular, the heat generated by the plurality of X-ray detector modules 100-1 to 100-*n* is discharged to the outside of the gantry 300 via the first module connection frame 210, and may be transferred to the gantry 300 via the second module connection frame 220. Therefore, a rise in a temperature of the plurality of X-ray detector modules 100-1 to 100-*n* may be prevented.

Figure 7B:
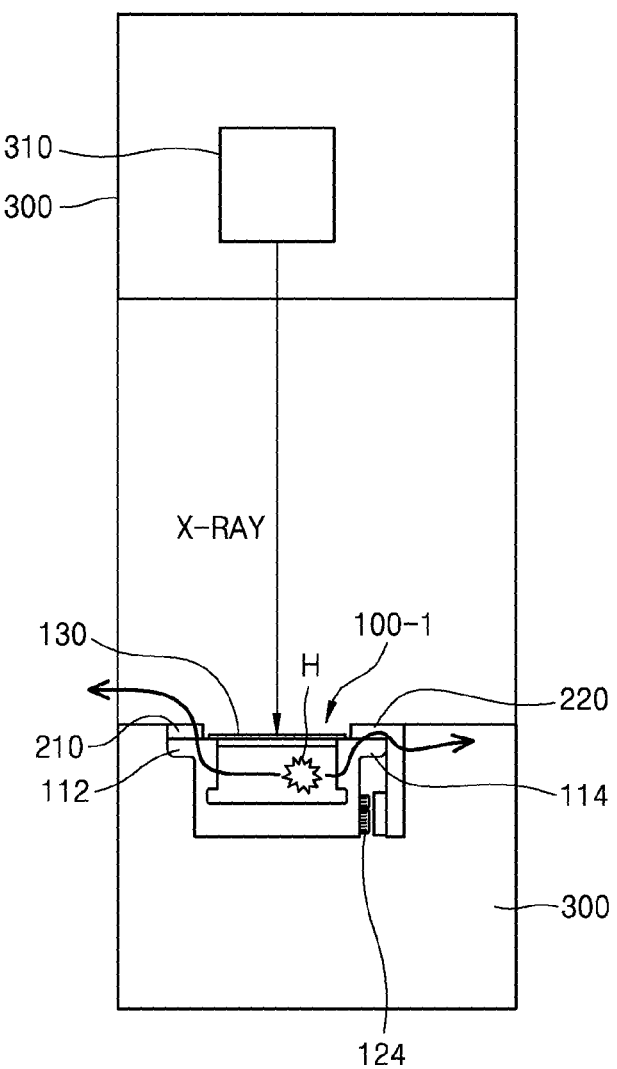
FIG. 7B is a conceptual diagram illustrating a structure in a CT system, according to an exemplary embodiment.

FIG. 7B illustrates a structure of the CT system 1000, according to the present exemplary embodiment. FIG. 7B is a cross-sectional view of the gantry 300 which includes the X-ray generator 310 of FIG. 7A.

Referring to FIG. 7B, the X-ray detector module 100-1 may be disposed on a location so as to face the X-ray generator 310 in the gantry 300. The X-ray detector module 100-1 may detect the X-ray generated by the X-ray generator 310. The first coupling joint 112 may be coupled to the first module connection frame 210, and the second coupling joint 114 may be coupled to the second module connection frame 220. In an exemplary embodiment, the second module connection frame 220 may be connected to the gantry 300. Heat H generated by the X-ray detector module 100-1 may be discharged to the outside of the gantry 300 through the first module connection frame 210, or may be transferred to the gantry 300 through the second module connection frame 220.

Figure 8:
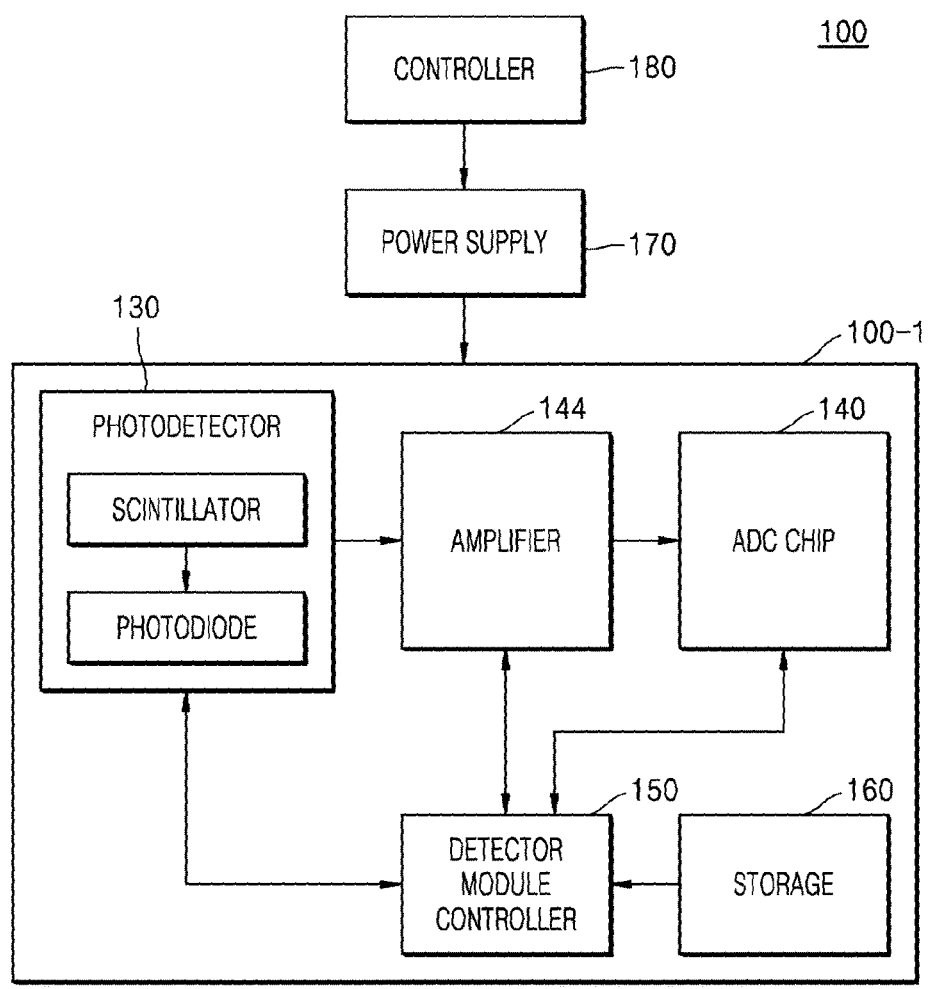
FIG. 8 is a block diagram showing elements in an X-ray detecting apparatus, according to an exemplary embodiment.

FIG. 8 is a block diagram of the X-ray detecting apparatus 100, according to the present exemplary embodiment.

Referring to FIG. 8, the X-ray detecting apparatus 100 includes the X-ray detector module 100-1, the power supply 170, and a controller 180. In FIG. 8, the X-ray detecting apparatus 100 includes one X-ray detector module 100-1 for convenience of description, but the X-ray detecting apparatus 100 may include the plurality of X-ray detector modules 100-1 to 100-*n*.

The X-ray detector module 100-1 may include the photodetector 130, the ADC chip 140, an amplifier 144, the detector module controller 150, and a storage 160.

The photodetector 130 receives the X-ray generated by the X-ray generator 310 (see FIGS. 1 and 2), and converts the X-ray into an electric signal. The photodetector 130 may include the scintillator 132, which is configured to react with the X-ray irradiated from the X-ray generator 310 toward the object 10 (see FIG. 1) so as to discharge photons having a wavelength of a visible frequency band, and the photodiode 134, which is configured to convert the photons discharged from the scintillator 132 into analog electric signals. Since the photodetector 130 is equivalent to the photodetector 130 described above with reference to FIG. 2, detailed descriptions thereof are omitted.

The ADC chip 140 converts the analog signal that has been converted by the photodetector 130 into a digital signal, and transmits the digital signal to the image processor 430 via the data transmitter 410 (see FIG. 2). The ADC chip 140 may include at least one of a CPU, a microprocessor, and a GPU that has a computational function of converting analog signals to digital signals.

The amplifier 144 may amplify the analog signal converted by the light receiving portion 130, and transmit an amplified signal to the ADC chip 140.

The detector module controller 150 may control operations of the light receiving portion 130, the ADC chip 140, and the amplifier 144. In an exemplary embodiment, the digital module controller 150 may correct setting parameter values that relate to a scan of the X-ray detector module 100-1. The setting parameter values for scan may include information that relate to at least one from among an offset calibration of the X-ray detector module 100-1 and a feedback capacitor of the X-ray detector module 100-1. Correction of the setting parameter values for scan will be described below with reference to FIGS. 13 and 14.

In an exemplary embodiment, the storage 160 may store information that relates to the offset calibration of the X-ray detector module 100-1 and the feedback capacitor of the X-ray detector module 100-1. In an exemplary embodiment, the detector module controller 150 receives the setting parameter values for scan from the storage 160, and may correct an offset value and/or a feedback capacitor value of the X-ray detector module 100-1.

In FIG. 8, the storage 160 is connected to the detector module controller 150, but is not limited thereto. In an exemplary embodiment, the storage 160 may be included in the ADC chip 140. The storage 160 may include, for example, at least one of a flash memory, a hard disk, a multimedia card micro type, a card type memory (SD, XD memory, etc.), a random access memory (RAM), a static RAM (SRAM), a read only memory (ROM), an electrically erasable programmable ROM (EEPROM), a programmable ROM (PROM), a magnetic memory, a magnetic disk, and an optical disk.

The power supply 170 may supply electric power to the X-ray detector module 100-1. The power supply 170 may be configured to have a plurality of channels, and may supply the electric power to the plurality of X-ray detectors 100-1 to 100-*n* (see FIGS. 6A and 7A) via the plurality of channels.

The controller 180 is connected to the power supply 170, and may control the power supply 170 to supply the electric power to the X-ray detector module 100-1 during an execution of an X-ray tomography scan. In FIG. 8, the X-ray detector module 100-1 is only shown for convenience of description, but the controller 180 may control the electric power supplied to the plurality of X-ray detector modules 100-1 to 100-*n* (see FIGS. 6A and 7A).

The controller 180 receives a signal for starting an X-ray tomography scan with respect to the X-ray detector module 100-1. In addition, when the X-ray tomography scan starts based on a reception of the signal for starting the X-ray tomography scan, the controller 180 supplies the electric power to the X-ray detector module 100-1, and when the X-ray tomography scan is completed, the controller 180 may terminate the supplying of the electric power to the X-ray detector module 100-1. In an exemplary embodiment, controller 180 may sense whether to start the X-ray tomography scan, based on a user input that relates to starting a scan which is received via the input unit 440 (see FIG. 2). In an exemplary embodiment, the controller 180 recognizes one or more changes in an external environment of the X-ray detecting apparatus 100 and senses whether to start the X-ray tomography scan via the recognized changes in the external environment. For example, the controller 180 may sense whether to start the X-ray tomography scan based on a variation in a voltage or a current supplied to the X-ray generator 310, or may sense whether to start the X-ray tomography scan based on a rotation of the gantry 300.

When the X-ray tomography scan is completed, the controller 180 may control the power supply 170 to terminate the supplying of the electric power to the X-ray detector module 100-1. For example, the controller 180 recognizes that the X-ray tomography scan has finished when X-ray data set in advance is acquired, and controls the power supply 170 to discontinue the supply of the electric power to the X-ray detector module 100-1.

In a conventional X-ray detector, the electric power has to be supplied to the X-ray detector in order to stabilize an offset level of the tomography image obtained via the X-ray tomography scan, and accordingly, the X-ray detector consumes a relatively large amount of power and generates a relatively large amount of heat. In particular, in the X-ray detector modules included in the X-ray detector, a leakage current of a semiconductor configuring the photodiode typically increases because an internal temperature of the X-ray detector increases, and accordingly, the offset level of the image tends to increase. Therefore, an image of high quality may be obtained when the X-ray tomography scan is performed only after the internal temperature of the X-ray detector is saturated to a predetermined temperature level or higher. However, in order to maintain the internal temperature of the X-ray detector at a predetermined level or higher, the X-ray detector must be in a standby mode even when the X-ray tomography scan is not performed, and since the electric power is continuously supplied during the standby time, the X-ray detector is aged due to the heat generation.

According to the X-ray detecting apparatus 100 of the exemplary embodiment, the electric power is supplied to the plurality of X-ray detector modules 100-1 to 100-n when the X-ray tomography scan starts, and when the X-ray tomography scan is finished, the electric power supplied to the plurality of X-ray detector modules 100-1 to 100-n is terminated so that the power consumption may be minimized, the heat generation from the plurality of X-ray detector modules 100-1 to 100-n is restrained, and deterioration of the X-ray detecting apparatus 100 may be prevented.

Figure 9:
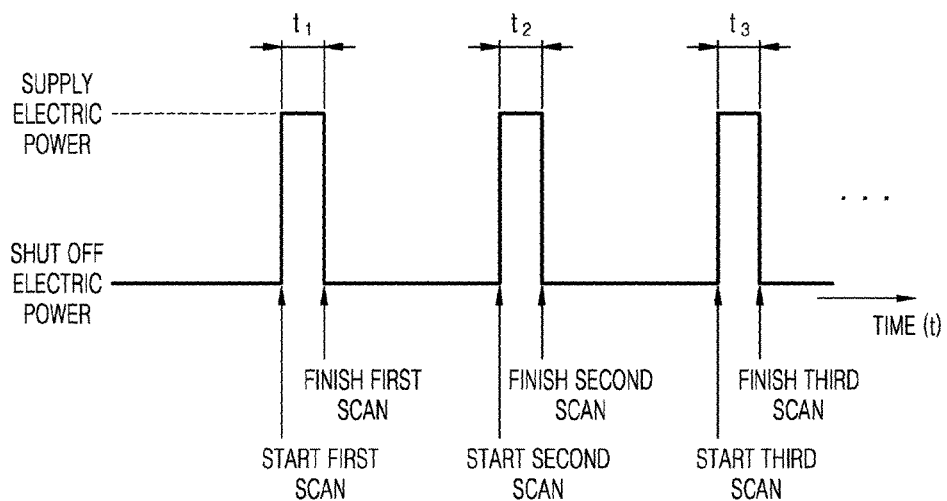
FIG. 9 is a diagram illustrating a method for supplying electric power to an X-ray detector module, according to an exemplary embodiment.

FIG. 9 is a diagram illustrating a method for supplying electric power to the plurality of X-ray detector modules 100-1 to 100-n, according to the present exemplary embodiment.

Referring to FIG. 9, when a signal for starting a first scan is received, the electric power is supplied to the plurality of X-ray detector modules 100-1 to 100-n, and when the first scan is completed, the electric power supplied to the plurality of X-ray detector modules 100-1 to 100-n may be terminated. When the first scan is completed, the electric power supplied to the plurality of X-ray detector modules 100-1 to 100-n may be terminated during a standby time period from the finish of the first scan to a point when a second scan starts. Likewise, when the second scan starts, the electric power is supplied to the plurality of X-ray detector modules 100-1 to 100-n, and when the second scan is completed, the electric power supplied to the plurality of X-ray detector modules 100-1 to 100-n may be terminated.

In FIG. 9, first, second, and third scans may be sequences for photographing different objects. In an exemplary embodiment, the first, second, and third scans may be sequences performed under different respective photograph protocols.

In FIG. 9, the first scan may be performed for a first time period $t_1$. Likewise, the second scan may be performed for a second time period $t_2$, and the third scan may be performed for a third time period $t_3$.

Although a driving method varies based on the CT system 1000, the X-ray detecting apparatus 100 generally consumes an electric power that falls within a range of between 1.2 kW per hour and 1.5 kW per hour. In the X-ray detecting apparatus 100 according to the present exemplary embodiment, the electric power is supplied to the plurality of X-ray detector modules 100-1 to 100-n only when the X-ray tomography scan is being performed, and when the X-ray tomography scan is finished, the electric power supplied to the plurality of X-ray detector modules 100-1 to 100-n is terminated so that a power consumption of 1 kW or greater per hour may be saved. For example, when it is assumed that a patient is examined for five to ten minutes on average, and a time duration of an X-ray tomography scan of a chest or an abdomen that is most frequently photographed, that is, the first time period t1 or the second time period t2, is ten seconds, a time duration in which the X-ray detecting apparatus 100 receives the power supply is twenty seconds, that is, only about 3.3% to 6.6% of the entire examination time period, that is, 300 seconds. Therefore, according to the present exemplary embodiment, the power consumption of the X-ray detecting apparatus 100 may be greatly reduced, and lifespan of the X-ray detecting apparatus 100 may be prolonged.

Figure 10:
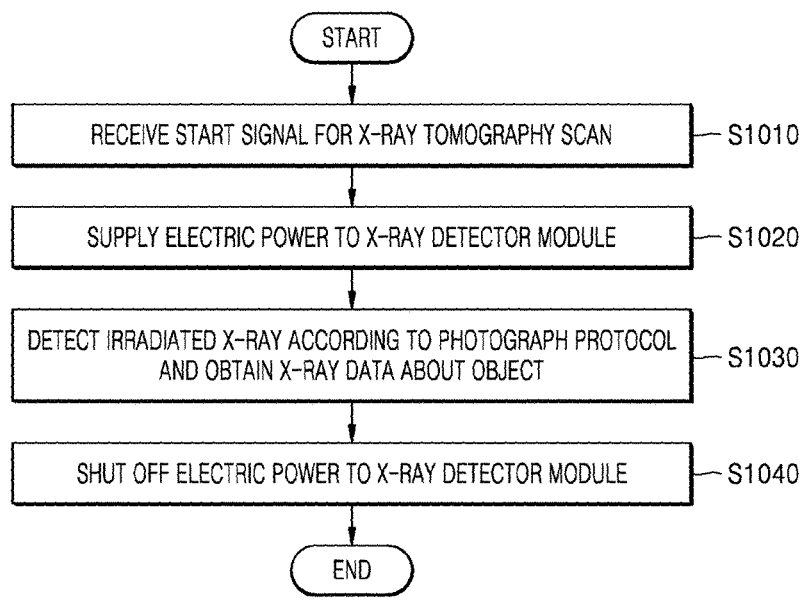
FIG. 10 is a flowchart illustrating a method for controlling a supply of electric power in an X-ray detecting apparatus, according to an exemplary embodiment.

FIG. 10 is a flowchart illustrating a method for controlling a supply of electric power with respect to the X-ray detecting apparatus 100, according to an exemplary embodiment.

In operation S1010, the X-ray detecting apparatus 100 receives a signal for starting an X-ray tomography scan. In an exemplary embodiment, the X-ray detecting apparatus 100 may sense whether to start the X-ray tomography scan by receiving a user input that relates to starting the X-ray tomography scan from a controller 400 (see FIG. 2) connected to the X-ray generator 310 (see FIG. 2), or from an external system (e.g., a console PC) that controls protocols of the X-ray tomography scan.

In operation S1020, the X-ray detecting apparatus 100 supplies electric power to X-ray detector modules. In an exemplary embodiment, the X-ray detecting apparatus 100 may not supply the electric power to the X-ray detector module, if the signal for starting the X-ray tomography scan is not received.

In operation S1030, the X-ray detecting apparatus 100 may detect an X-ray irradiated according to photographing protocols, and obtains X-ray data regarding an object. In an exemplary embodiment, the X-ray detecting apparatus 100 receives the X-ray irradiated onto the object from the X-ray generator 310 (see FIG. 2) in order o output photons that have a wavelength of a visible frequency band, and converts the photons into an electric signal in order to obtain the X-ray data relating to the object.

In operation S1040, the X-ray detecting apparatus 100 terminates the supplying of the electric power to the X-ray detector module. In an exemplary embodiment, the X-ray detecting apparatus 100 recognizes that the X-ray tomography scan is completed, and then terminates the supply of the electric power to the X-ray detector module.

Figure 11:
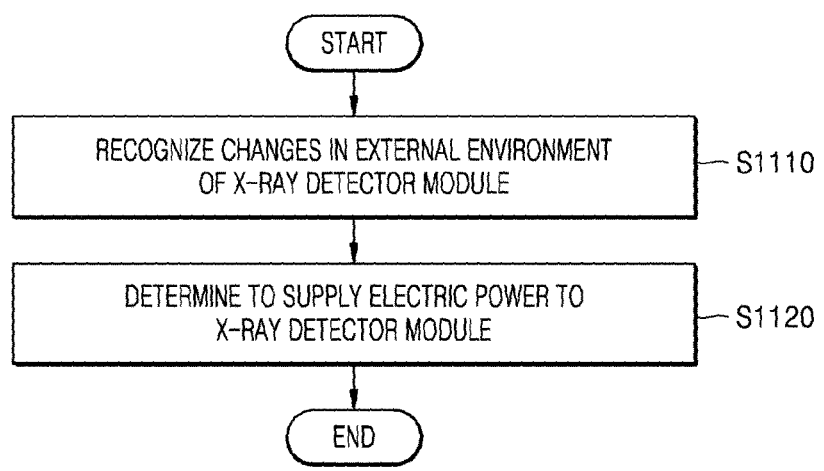
FIG. 11 is a flowchart illustrating a method for controlling a supply of electric power in an X-ray detecting apparatus, according to an exemplary embodiment.

FIG. 11 is a flowchart illustrating a method for controlling a supplying of electric power in the X-ray detecting apparatus 100, according to an exemplary embodiment.

In operation S1110, the X-ray detecting apparatus 100 recognizes one or more changes in an external environment of an X-ray detector module. In an exemplary embodiment, the X-ray detecting apparatus 100 may include a sensor configured for sensing a temperature, a pressure, and/or a wind direction around the X-ray detector module, and may sense a temperature of the X-ray detector module, a pressure applied to the X-ray detector module, and a direction and a strength of wind blowing to the X-ray detector module by using the sensor. In an exemplary embodiment, the X-ray detecting apparatus 100 may recognize whether to start an X-ray tomography scan via a variation in a voltage or a current supplied to the X-ray generator 310 (see FIG. 2).

In operation S1120, the X-ray detecting apparatus 100 may determine whether to supply the electric power to the X-ray detector module according to a change in the external environment. In an exemplary embodiment, the X-ray detecting apparatus 100 may sense a strength of wind blowing to the X-ray detector module. When the strength of the wind is equal to a critical value that is set in advance or greater, the X-ray detecting apparatus 100 recognizes that the gantry 300 to which the X-ray detecting apparatus 100 is connected is rotating, and thereby initiates the supply of the electric power to the X-ray detector module. When the strength of the wind blowing to the X-ray detector module is less than a critical value, the X-ray detecting apparatus 100 recognizes that the rotation of the gantry 300 has stopped, and terminates the supply of the electric power to the X-ray detector module.

Figure 12:
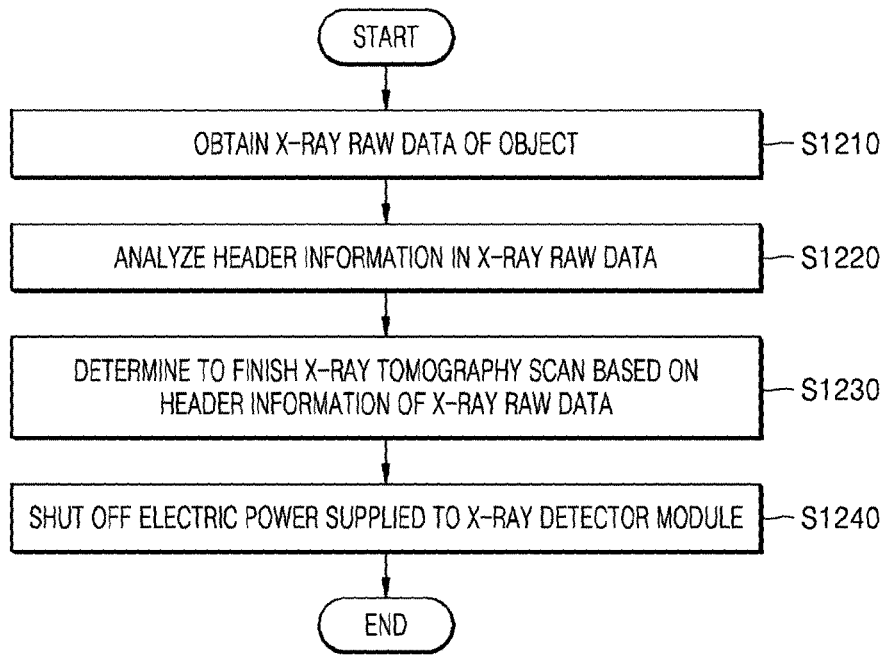
FIG. 12 is a flowchart illustrating a method for controlling a supply of electric power in an X-ray detecting apparatus, according to an exemplary embodiment.

FIG. 12 is a flowchart illustrating a method for controlling the supplying of electric power in the X-ray detecting apparatus 100, according to an exemplary embodiment.

In operation S1210, the X-ray detecting apparatus 100 acquires X-ray raw data that relates to an object. In an exemplary embodiment, the X-ray detecting apparatus 100 detects the X-ray irradiated from the X-ray generator 310 (see FIG. 2) toward the object, and then converts the X-ray into an electric signal in order to obtain the X-ray raw data. The X-ray raw data denotes data converted by the X-ray detecting apparatus 100 and not yet processed by the image processor 430 (see FIG. 2).

In operation S1220, the X-ray detecting apparatus 100 analyzes header information of the X-ray raw data. In an exemplary embodiment, the X-ray detecting apparatus 100 analyzes the header information of the X-ray raw data, and may recognize an X-ray tomography scanning protocol, a scanning sequence, and the number of X-ray tomography images from the header information.

In operation S1230, the X-ray detecting apparatus 100 determines whether to stop the X-ray tomography scanning based on the header information of the X-ray raw data. In an exemplary embodiment, the X-ray detecting apparatus 100 may identify the number of tomography images from the information included in the header information of the X-ray raw data. When the number of the tomography images matches the information included in the header information of the X-ray raw data, the X-ray detecting apparatus 100 may determine that the X-ray tomography scanning to be completed. In an exemplary embodiment, the X-ray detecting apparatus 100 may determine to finish the X-ray tomography scan when the X-ray tomography scanning protocols included in the header information of the X-ray raw data have been all scanned.

In operation S1240, the X-ray detecting apparatus 100 terminates the supply of the electric power to the X-ray detector module.

Figure 13:
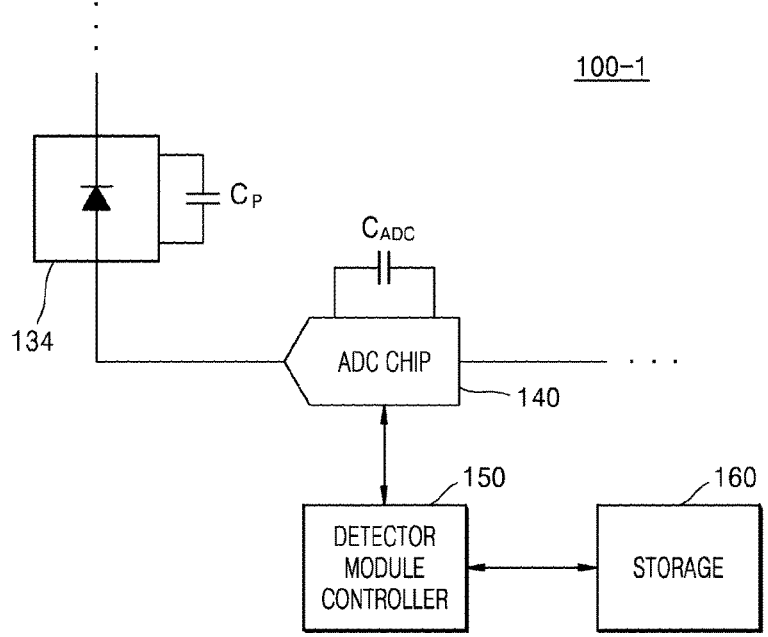
FIG. 13 is a block diagram illustrating a method for correcting a setting parameter value for scan of an X-ray detector module, according to an exemplary embodiment.

FIG. 13 is a block diagram illustrating a method for correcting a setting parameter value for scan of the X-ray detector module 100-1, according to an exemplary embodiment.

Referring to FIG. 13, the X-ray detector module 100-1 may include the photodiode 134, the ADC chip 140, the detector module controller 150, and the storage 160.

The photodiode 134 may include a plurality of semiconductor devices. When the electric power is supplied to the X-ray detector module 100-1, the ADC chip 140 and the detector module controller 150 generate heat, and thus, a temperature of the X-ray detector module 100-1 may rise. In this case, leakage currents from the plurality of semiconductor devices included in the photodiode 134 may increase, and a capacitor ($C_P$) value of the photodiode 134 varies. Accordingly, offset values of the tomography images obtained via the X-ray tomography scan may not be constant. Therefore, when the temperature of the X-ray detector module 100-1 rises, the detector module controller 150 receives setting parameter values for scan from the storage 160 in order to correct the offset values by using the setting parameter values for scan. In an exemplary embodiment, the setting parameter values for scan may include an offset calibration value for correcting obtained tomography images according to the temperature of the photodiode 134 based on a dark image that is obtained while the X-ray is not irradiated onto the X-ray detector module 100-1, and a gain value of a feedback capacitor for matching the capacitor $C_P$ of the photodiode 134 with a capacitor $C_{ADC}$ of the ADC chip 140. In an exemplary embodiment, the storage 160 may store information that relates the offset calibration value and the gain value of the feedback capacitor.

In general, the X-ray detector stands-by for a predetermined time period so that temperatures of components in the X-ray detector including the ADC chip 140 and the detector module controller 150 may be saturated to a predetermined temperature or higher, and corrects the offset value by using the setting parameter value when the temperature of the X-ray detector is saturated to a predetermined temperature or greater. If the X-ray scan is performed while the temperature of the X-ray detector is rising before being saturated at the predetermined temperature, a difference between the offset levels of the photographed image and the dark image may affect the quality of the tomography image.

In this aspect, the X-ray detecting apparatus 100 according to the present exemplary embodiment receives setting parameter values from the storage 160 when a signal for starting the X-ray tomography scan is transmitted, and may correct the offset value based on the received setting parameter values. In particular, since the offset value is corrected when the X-ray tomography scan starts, there is no need to stand by until the temperature of the X-ray detector module rises up to a predetermined level or higher; instead, the X-ray tomography scan may be performed at a relatively low temperature.

Figure 14:
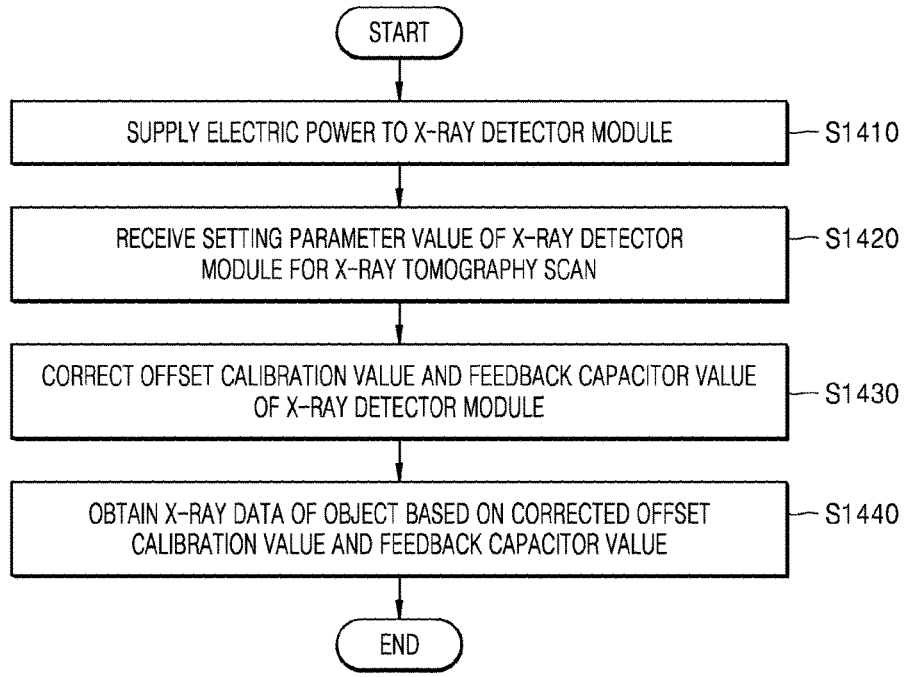
FIG. 14 is a flowchart illustrating a method for operating an X-ray detecting apparatus, wherein the method includes correcting a setting parameter value for scan of an X-ray detector module, according to an exemplary embodiment.

FIG. 14 is a flowchart illustrating a method for operating the X-ray detecting apparatus 100, wherein the method includes correcting an offset value of the X-ray detector module, according to an exemplary embodiment.

In operation S1410, the X-ray detecting apparatus 100 supplies an electric power to the X-ray detector module. In an exemplary embodiment, the X-ray detecting apparatus 100 may supply the electric power to the X-ray detector module after receiving a signal for starting the X-ray tomography scan.

In operation S1420, the X-ray detecting apparatus 100 receives a setting parameter value of the X-ray detector module for performing the X-ray tomography scan. In an exemplary embodiment, the setting parameter value may include an offset calibration value for correcting the offset value of the X-ray detector module based on a dark image, and a gain value of a feedback capacitor. In an exemplary embodiment, the X-ray detecting apparatus 100 may receive information that relates to the offset calibration value and the gain value of the feedback capacitor from the storage 160.

In operation S1430, the X-ray detecting apparatus 100 corrects the offset calibration value and the gain value of the feedback capacitor of the X-ray detector module.

In operation S1440, the X-ray detecting apparatus 100 obtains X-ray data that relates to an object based on the corrected offset calibration value and corrected feedback capacitor value.

In an exemplary embodiment, the X-ray detecting apparatus 100 may terminate the supplying of the electric power to the X-ray detector module after obtaining the X-ray data.

The exemplary embodiments can be written as computer programs and can be implemented in general-use digital computers that execute the programs using a computer readable recording medium. Examples of the computer readable recording medium include magnetic storage media (e.g., read-only memory (ROM), floppy disks, hard disks, etc.), optical recording media (e.g., compact disk-ROM (CD-ROMs), or digital versatile disks (DVDs)), and/or any other suitable medium.

While one or more exemplary embodiments have been described with reference to the figures, it will be understood by those of ordinary skill in the art that various changes in form and details may be made therein without departing from the spirit and scope as defined by the following claims.

What is claimed is:

1. An X-ray detecting apparatus comprising at least one X-ray detector module configured to detect an X-ray irradiated from an X-ray generator toward an object in order to obtain X-ray data relating to the object,
    wherein the at least one X-ray detector module comprises:
    a body that includes a metal material;
    a photodetector disposed at a side of the body and configured to receive the X-ray irradiated from the X-ray generator and to convert an X-ray signal into an electric signal;
    a first circuit board disposed on a first surface of the body, the first surface of the body having an orientation that is orthogonal to the side of the body at which the photodetector is disposed;
    a first analog/digital converter (ADC) chip mounted on an upper surface of the first circuit board and configured to convert the electric signal into a digital signal; and
    a thermal pad interposed between the first surface of the body and an upper surface of the first ADC chip,
    wherein an upper surface of the first circuit board is further disposed to face the first surface of the body.

2. The X-ray detecting apparatus of claim 1, wherein the at least one X-ray detector module further comprises:
    a second circuit board disposed on a second surface of the body, wherein the second surface is opposite to the first surface;
    a second ADC chip mounted on an upper surface of the second circuit board; and
    a thermal pad interposed between the second surface of the body and the second ADC chip.

3. The X-ray detecting apparatus of claim 1, wherein the photodetector comprises:
    a scintillator configured to receive the X-ray irradiated from the X-ray generator, and to discharge the received X-ray as photons of a visible frequency band; and
    a photodiode configured to convert the photons into an analog electric signal,
    wherein the photodiode is disposed at a side of the body and the scintillator is disposed on an upper surface of the photodiode.

4. The X-ray detecting apparatus of claim 3, wherein the at least one X-ray detector module further comprises a plurality of X-ray detector modules which are arranged in an array, and the X-ray detecting apparatus further comprises a module connection frame configured for connecting the plurality of X-ray detector modules to each other.

5. The X-ray detecting apparatus of claim 4, wherein the body comprises a first coupling joint that extends from the side of the body, at which the photodetector is disposed, so as to protrude in a first direction, and a second coupling joint that extends from the side of the body so as to protrude in a second direction that is opposite to the first direction, and
    the module connection frame comprises a first frame coupled to the first coupling joint and a second frame coupled to the second coupling joint.

6. The X-ray detecting apparatus of claim 4, wherein the plurality of X-ray detector modules are installed in a gantry that is configured to rotate, and wherein each of the plurality of X-ray detector modules is disposed to face the X-ray generator that is installed in the gantry.

7. An X-ray detecting apparatus comprising:
    at least one X-ray detector module configured to detect an X-ray irradiated from an X-ray generator toward an object, and to convert the detected X-ray into an electric signal based on a photograph protocol which relates to obtaining X-ray data about the object;
    a power supply configured to supply electric power to the at least one X-ray detector module;
    a memory configured to store a setting parameter value that comprises an offset value of the at least one X-ray detector module; and
    a controller configured to receive a signal for starting an X-ray tomography scan with respect to the at least one X-ray detector module, and to control the power supply to automatically supply the electric power to the at least one X-ray detector module, to turn the at least one X-ray detector module on when an X-ray tomography scan starts based on the received signal and to terminate the supplying of the electric power to the at least one X-ray detector module, and to shut off electric power to the at least one X-ray detector module when the X-ray tomography scan is determined to be completed based on information included in the obtained X-ray data,
    wherein the controller is further configured to receive the setting parameter value from the memory and perform an offset calibration based on the offset value comprised in the received setting parameter value after supplying the electric power to the at least one X-ray detector module.

8. The X-ray detecting apparatus of claim 7, wherein the controller is further configured to control the power supply to terminate a supplying of the electric power to the at least one X-ray detector module, without having received the signal for starting the X-ray tomography scan.

9. The X-ray detecting apparatus of claim 7, wherein the controller is further configured to recognize at least one change in an external environment of the at least one X-ray detector module, and to control the power supply to supply electric power to the at least one X-ray detector module or to terminate a supplying of the electric power to the at least one X-ray detector module based on the recognized at least one change in the external environment of the at least one X-ray detector module.

10. The X-ray detecting apparatus of claim 7, wherein the at least one X-ray detector module is further configured to acquire an X-ray raw data image of the object, and the controller is further configured to determine that the X-ray tomography scan is completed by analyzing header information included in the X-ray raw data image and to control the power supply to terminate the supplying of the electric power to the at least one X-ray detector module based on the determination.

11. The X-ray detecting apparatus of claim 7, wherein the setting parameter value further comprises information that relates to a feedback capacitor included in the at least one X-ray detector module.

12. The X-ray detecting apparatus of claim 11, wherein the at least one X-ray detector module further comprises a detector module controller configured for correcting, based on the stored setting parameter value, at least one from among an offset value of the at least one X-ray detector module and a feedback capacitor value.

13. The X-ray detecting apparatus of claim 12, wherein the detector module controller is further configured to receive the setting parameter value from the storage when an X-ray tomography scan starts based on a reception of a signal for starting the X-ray tomography scan.

14. A method for operating an X-ray detecting apparatus comprising at least one X-ray detector module configured to detect an X-ray irradiated from an X-ray generator toward an object and to obtain X-ray data that relates to the object, the method comprising:
receiving a signal for starting an X-ray tomography scan;
in response to the received signal, automatically supplying electric power to the at least one X-ray detector module and turning the at least one X-ray detector module on;
receiving a setting parameter value that comprises an offset value of the at least one X-ray detector module;
performing an offset calibration based on the offset value comprised in the received setting parameter value;
detecting an X-ray irradiated toward the object based on a photograph protocol that relates to obtaining X-ray data of the object; and
terminating the supplying of the electric power to the at least one X-ray detector module and shutting off electric power to the at least one X-ray detector module when the X-ray tomography scan is determined to be completed based on information included in the obtained X-ray data.

15. The method of claim 14, further comprising terminating the supplying of the electric power to the at least one X-ray detector module, before receiving the signal for starting the X-ray tomography scan.

16. The method of claim 14, wherein the receiving the signal for starting the X-ray tomography scan comprises:
recognizing at least one change in an external environment of the at least one X-ray detector module; and
determining whether to initiate or terminate a supplying of the electric power to the at least one X-ray detector module based on the recognized at least change in the external environment.

17. The method of claim 14, wherein the obtaining the X-ray data comprises obtaining X-ray raw data that relates to the object, and
the terminating the supplying of the electric power to the at least one X-ray detector module comprises:
determining that the X-ray tomography scan is completed by analyzing header information that relates to the X-ray raw data; and
terminating the supplying of the electric power to the at least one X-ray detector module based on a result of the determining.

18. The method of claim 14, wherein the received setting parameter value comprises information that relates to at least one from among an offset calibration of the at least one X-ray detector module and a feedback capacitor included in the at least one X-ray detector module, and wherein the method further comprises correcting at least one from among an offset value of the at least one X-ray detector module and a feedback capacitor value, based on the received setting parameter value.

* * * * *